US012681197B2

(12) United States Patent
Choi

(10) Patent No.: US 12,681,197 B2
(45) Date of Patent: Jul. 14, 2026

(54) FLEXIBLE DETECTOR AND IMAGING DEVICE INCLUDING THE SAME

(71) Applicant: Vieworks Co., Ltd., Anyang-si (KR)

(72) Inventor: Jung Min Choi, Ansan-si (KR)

(73) Assignee: Vieworks Co., Ltd., Anyang-si (KR)

( * ) Notice: Subject to any disclaimer, the term of this patent is extended or adjusted under 35 U.S.C. 154(b) by 166 days.

(21) Appl. No.: 18/641,617

(22) Filed: Apr. 22, 2024

(65) Prior Publication Data

US 2024/0272315 A1     Aug. 15, 2024

Related U.S. Application Data

(63) Continuation of application No. PCT/KR2022/015743, filed on Oct. 17, 2022.

(30) Foreign Application Priority Data

Oct. 21, 2021     (KR) ......................... 10-2021-0141227

(51) Int. Cl.
| | |
|---|---|
| *G01T 1/24* | (2006.01) |
| *A61B 6/00* | (2024.01) |
| *A61B 6/42* | (2024.01) |
| *G01N 23/04* | (2018.01) |
| *G01T 1/20* | (2006.01) |

(52) U.S. Cl.
CPC ............ *G01T 1/244* (2013.01); *A61B 6/4283* (2013.01); *A61B 6/4405* (2013.01); *G01N 23/043* (2013.01); *G01T 1/20189* (2020.05); *G01T 1/241* (2013.01); *G01N 2223/301* (2013.01)

(58) Field of Classification Search
CPC ... G01T 1/244; G01T 1/20189; A61B 6/4283; A61B 6/4405
See application file for complete search history.

(56) References Cited

U.S. PATENT DOCUMENTS

| | | |
|---|---|---|
| 11,061,153 B2 | 7/2021 | Jadrich et al. |
| 2010/0072379 A1 | 3/2010 | Nishino et al. |
| 2020/0194489 A1 | 6/2020 | Bert et al. |
| 2021/0190704 A1 | 6/2021 | Bogumil et al. |

(Continued)

FOREIGN PATENT DOCUMENTS

| | | |
|---|---|---|
| JP | 2003-344542 A | 12/2003 |
| JP | 2012-198246 A | 10/2012 |
| JP | 2015-180239 A | 10/2015 |

(Continued)

*Primary Examiner* — Casey Bryant
(74) *Attorney, Agent, or Firm* — Bridgeway IP Law Group, PLLC; Jihun Kim

(57)     ABSTRACT

Provided is a flexible detector and an imaging device including the same, which are capable of improving structural stability of the detector even in a state in which the detector changes in shape. A detector according to an embodiment includes a first part including a first housing made of an elastic material, and a detection panel provided in the first housing, a second part connected to the first part and including a second housing made of an inelastic material or a material having higher rigidity than the material of the first housing, and a reinforcement member disposed outside the detection panel and provided on the first housing so as to surround at least a part of the detection panel on a horizontal plane.

18 Claims, 27 Drawing Sheets

(56) References Cited

U.S. PATENT DOCUMENTS

2022/0133250 A1 * 5/2022 Reina .................. A61B 6/4291
378/164

FOREIGN PATENT DOCUMENTS

| JP | 2015225331 A | * | 12/2015 | |
|----|--------------|---|---------|--------------|
| JP | 2017036968 A | * | 2/2017 | ............ A61B 6/102 |
| KR | 10-2019-0042409 A | | 4/2019 | |
| KR | 10-2020-0001884 A | | 1/2020 | |
| KR | 10-2138745 B1 | | 7/2020 | |
| KR | 10-2021-0080242 A | | 6/2021 | |

* cited by examiner (a)

(c)                  (b)

(a)

(b)

(a)

(b)

(a)

(b)

(a)

(b)

FLEXIBLE DETECTOR AND IMAGING DEVICE INCLUDING THE SAME

CROSS-REFERENCE TO RELATED APPLICATIONS

This application is a continuation application of PCT International Application No. PCT/KR2022/015743 filed on Oct. 17, 2022, which claims the priority of Korean Patent Application No. 10-2021-0141227 filed on Oct. 21, 2021, the disclosure of which is incorporated herein by reference.

TECHNICAL FIELD

The present invention relates to a flexible detector and an imaging device including the same, and more particularly, to a flexible detector and an imaging device including the same, which are capable of improving structural stability of the detector even in a state in which the detector changes in shape.

BACKGROUND ART

A non-destructive testing method refers to a method that inspects materials, performance, states, whether a defect is present, and the like without destroying test targets.

The non-destructive testing method may be used to identify an internal structure or a defect without destroying the test target. For example, the non-destructive testing method may be used to inspect quality of various types of industrial products in industrial sites, identify whether buildings and the like are defective, and identify abrasion/corrosion states.

In case that non-destructive testing is performed by using X-rays among the non-destructive testing methods, a hollow cylindrical object, e.g., a pipe may be used as a test target. In case that the pipe is used as the test target, most of the methods have used analog-type films recently.

This is because the imaging process is performed after the film is tightly fixed to an outer peripheral surface of the pipe because the pipes, which are used as the test targets, have different radii.

Therefore, in case that the pipe is used as the test target, it is not easy to use a digital radiography detector (DR detector) that is a flat panel detector.

DISCLOSURE

Technical Problem

An object of the present invention is to provide a flexible detector and an imaging device including the same, which are capable of improving structural stability of the detector even in a state in which the detector changes in shape.

Another object of the present invention is to provide a flexible detector and an imaging device including the same, which are capable of allowing a detection panel, which is configured to detect radiation, to be easily and tightly attached to a test target.

Technical Solution

A detector according to an embodiment of the present invention includes a first part including a first housing made of an elastic material, and a detection panel provided in the first housing, a second part connected to the first part and including a second housing made of an inelastic material or a material having higher rigidity than the material of the first housing, and a reinforcement member disposed outside the detection panel and provided on the first housing so as to surround at least a part of the detection panel on a horizontal plane.

In the embodiment, the reinforcement member may include a connection portion coupled to one end of the second housing at which the first housing and the second housing are connected.

In the embodiment, the reinforcement member may be disposed over the first housing and the second housing.

In the embodiment, the reinforcement member may include a connection portion coupled to the inside of the second housing.

In the embodiment, the first housing may include: a panel accommodation portion configured to accommodate the detection panel; and a reinforcement member accommodation portion formed outside the panel accommodation portion when viewed on the horizontal plane, the reinforcement member accommodation portion being configured to accommodate the reinforcement member.

In the embodiment, the reinforcement member may include: a first reinforcement portion disposed in a first accommodation region of the reinforcement member accommodation portion in a first direction; and a second reinforcement portion disposed in a second accommodation region of the reinforcement member accommodation portion in a second direction perpendicular to the first direction, and the reinforcement member may be configured to move in the reinforcement member accommodation portion in the first or second direction on the horizontal plane when the first part is bent.

In addition, the first reinforcement portion may include a protruding portion protruding from one end in a vertical direction or protruding from one end so as to have a predetermined angle with respect to the vertical direction, the first accommodation region may include a stopper portion configured to come into contact with the protruding portion in the first direction when the first reinforcement portion moves in the first direction on the horizontal plane, and a state in which the first part is maximally bent in the first direction may be a state in which the protruding portion and the stopper portion are in contact with each other.

In the embodiment, the first housing may include: a first plate disposed on one surface of the reinforcement member; and a second plate disposed on the other surface of the reinforcement member opposite to one surface of the reinforcement member in a vertical direction.

In addition, the detector may further include: a bending restriction part configured to restrict a degree to which the first part is maximally bendable, in which the bending restriction part is disposed in a bending restriction part guide portion formed in the reinforcement member in a first direction on the horizontal plane, and in which the bending restriction part is configured to move in the first direction on the horizontal plane along the bending restriction part guide portion when the first part is bent.

In addition, the bending restriction part guide portion may be provided as a pair of bending restriction part guide portions disposed in a second direction perpendicular to the first direction with the detection panel interposed therebetween. In addition, the bending restriction part may include a protruding portion protruding from one end in the vertical direction or protruding from one end so as to have a predetermined angle with respect to the vertical direction, and the reinforcement member may include a stopper portion configured to come into contact with the protruding portion in the first direction when the bending restriction part moves in the first direction on the horizontal plane.

In the embodiment, the second part may include a first ring portion formed in a first direction, and a second ring portion formed in a second direction different from the first direction, and a fixing part configured to fix the detector to a test target may be coupled to the first ring portion and the second ring portion.

In addition, the first ring portion may be provided as a pair of first ring portions, the second ring portion may be provided as a pair of second ring portions, and the pair of first ring portions and the pair of second ring portions may be formed at positions at which the fixing part presses portions of the first housing disposed outside the detection panel.

In addition, a fixing block on which the first ring portion and the second ring portion are formed may be coupled to the second housing.

In addition, a third ring portion may be additionally provided at a side of the second housing opposite to the first part, and a branch portion, which branches off from the fixing part, may be coupled to the third ring portion. In the embodiment, a fixing part passage groove may be formed at a lateral end of the second housing, and a fixing part configured to fix the detector to a test target may pass through the fixing part passage groove.

In addition, the present invention provides an imaging device including: the detector; a fixing part configured to fix the detector so that the detector is tightly attached to a test target; and a radioactive ray generation part provided inside or outside the test target and configured to emit radiation to the detector.

In the embodiment, the imaging device may further include: an auxiliary board configured to press the first part of the detector toward the test target.

Advantageous Effects

According to the present invention, the reinforcement member is disposed over the housing made of an inelastic material and the housing made of an elastic material. When the housing made of the elastic material is tightly attached to the test target and changed in shape, a high tensile force is applied to the housing made of the elastic material and the detection panel provided in the housing made of the elastic material, which may prevent damage to the housing, which is made of the elastic material, and the detection panel. In addition, in case that the housing made of the elastic material changes in shape, the housing made of the elastic material may be prevented from being rapidly bent or folded by an external impact. In case that a radiographic inspection is not performed, the housing made of the elastic material may be immediately unfolded.

In addition, according to the present invention, the detection panel configured to detect radiation may be easily tightly attached to the test target.

MODE FOR INVENTION

Figure 1:
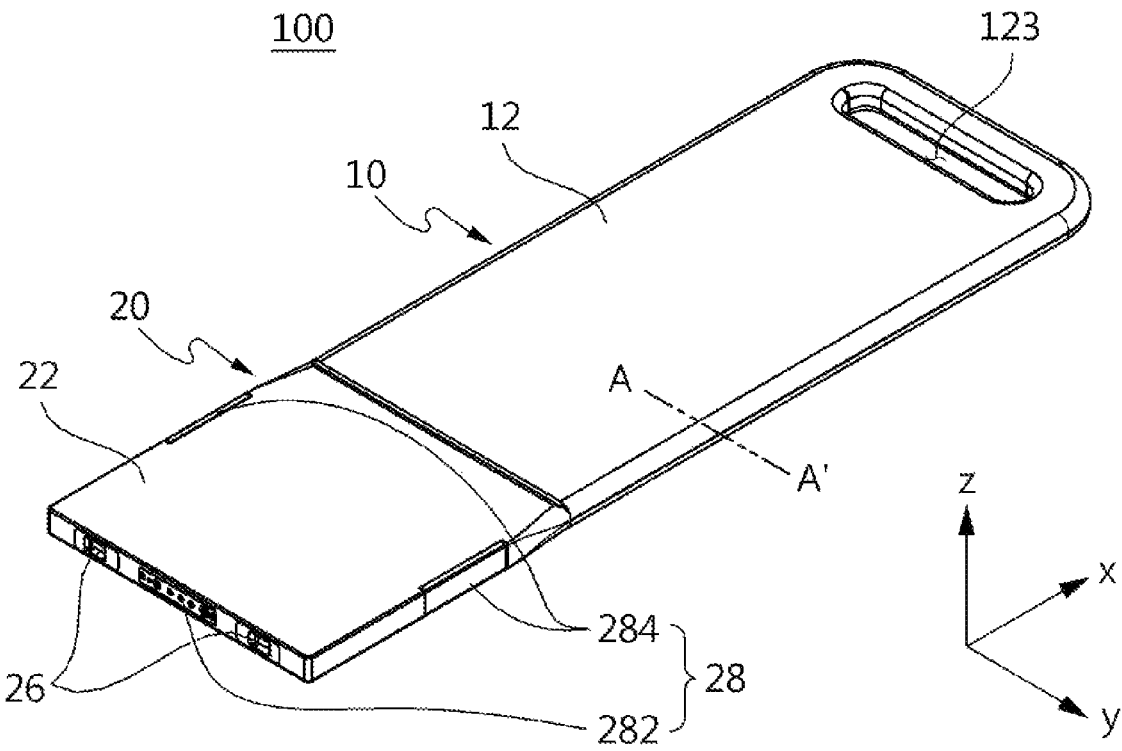
FIG. 1 is a perspective view of a detector according to a first embodiment of the present invention.

Hereinafter, exemplary embodiments of the present invention will be described in detail with reference to the accompanying drawings. First, in assigning reference numerals to constituent elements of the respective drawings, it should be noted that the same constituent elements will be designated by the same reference numerals, if possible, even though the constituent elements are illustrated in different drawings. In addition, in the description of the present invention, the specific descriptions of publicly known related configurations or functions will be omitted when it is determined that the specific descriptions may obscure the subject matter of the present invention. Further, the exemplary embodiments of the present invention will be described below, but the technical spirit of the present invention is not limited thereto and may of course be modified and variously carried out by those skilled in the art.

Figure 2:
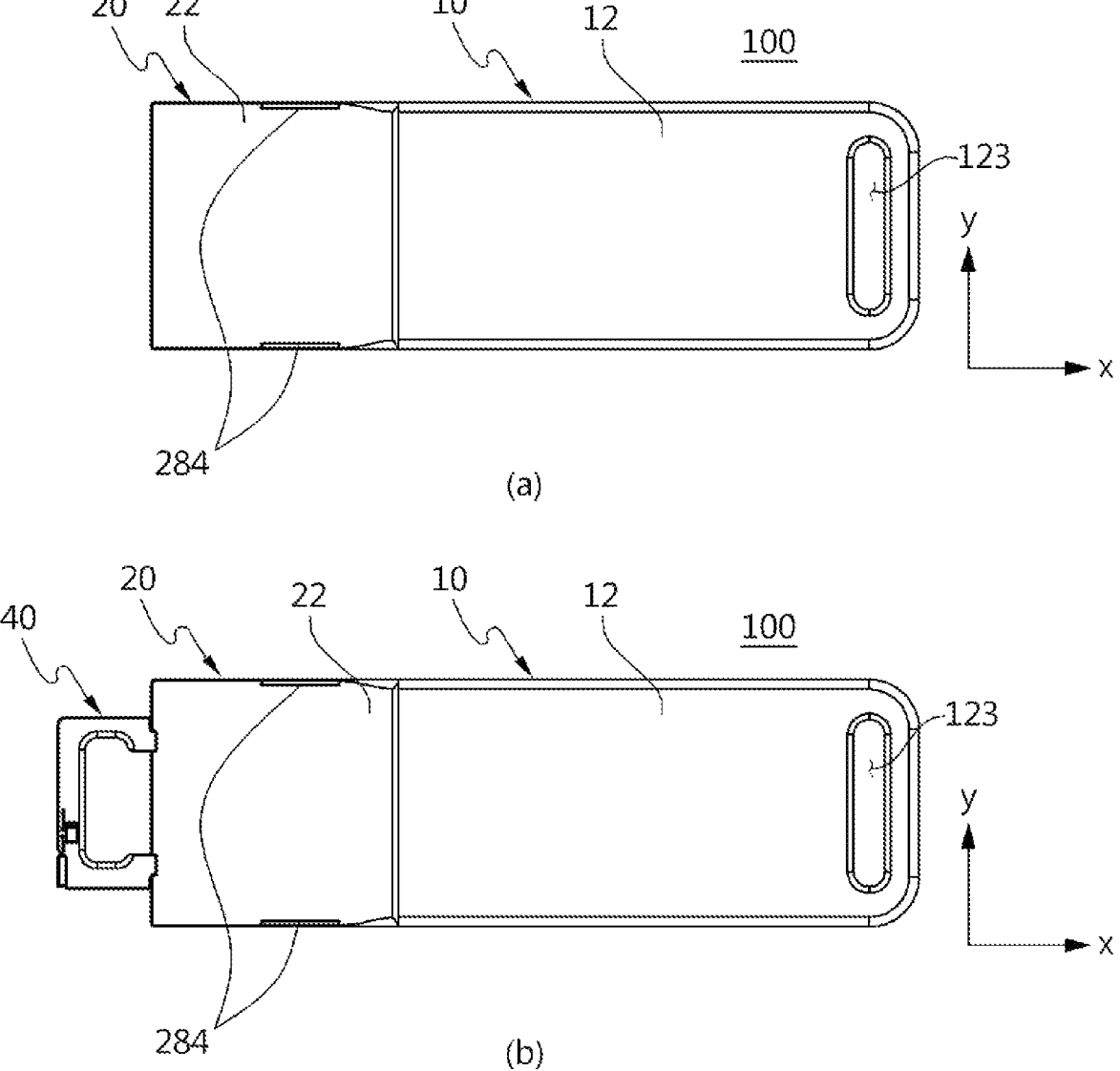
FIG. 2 is a view illustrating states made before and after a grip part is coupled to the detector according to the first embodiment of the present invention when viewed from above or below.
Figure 3:
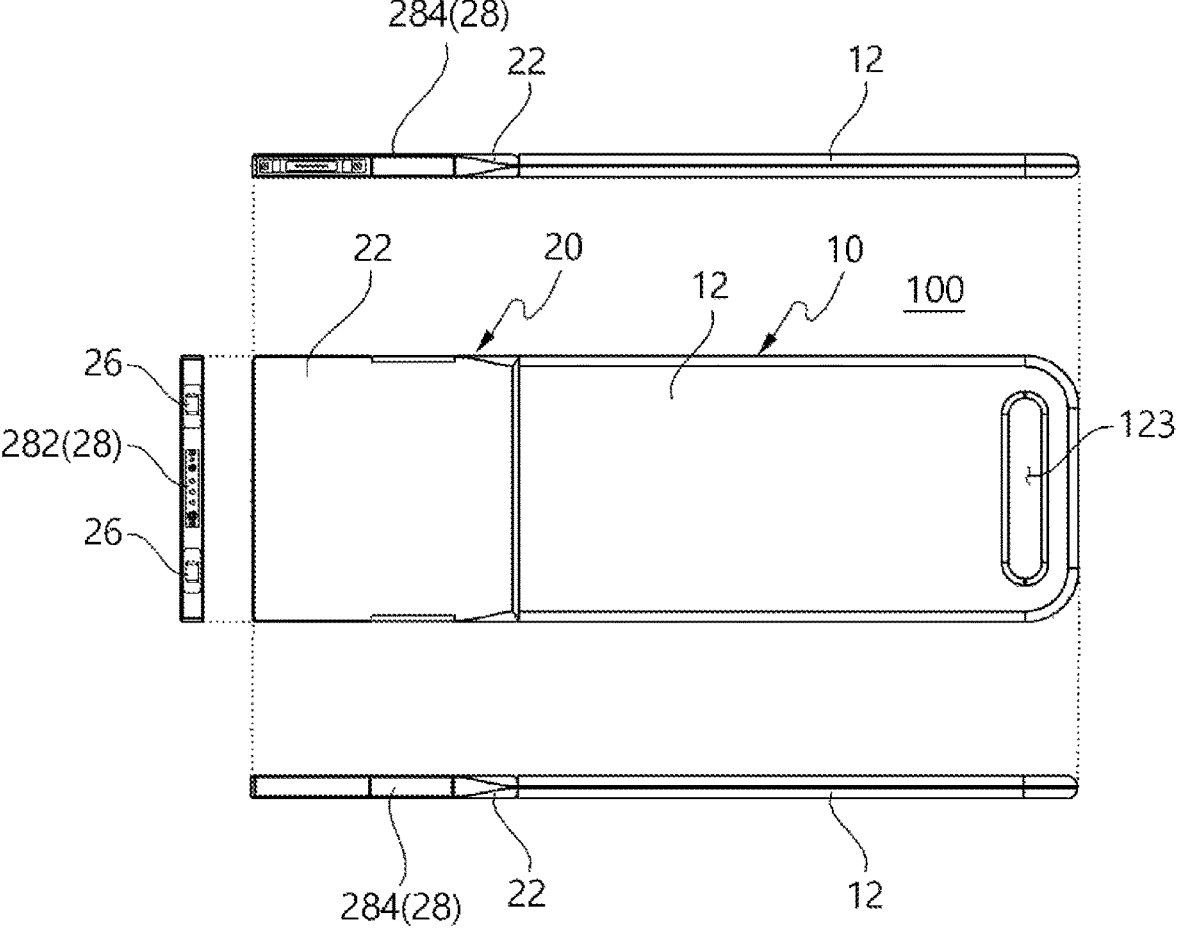
FIG. 3 is a view illustrating an upper surface, a lateral surface, and a rear surface of the detector according to the first embodiment of the present invention.
Figure 4:
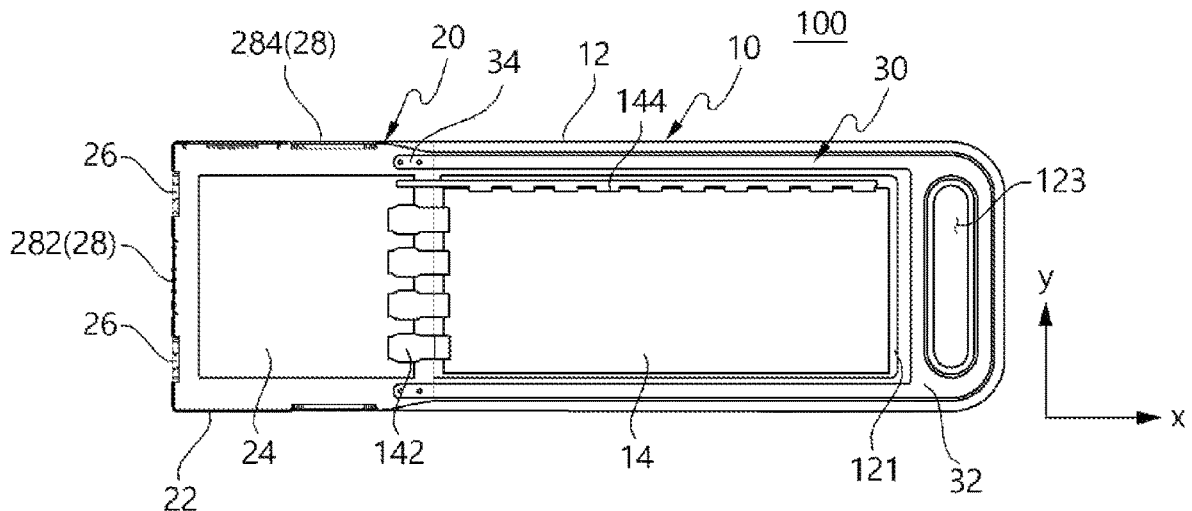
FIG. 4 is a transparent view illustrating the inside of the detector according to the first embodiment of the present invention.

FIG. 1 is a perspective view of a detector 100 according to a first embodiment of the present invention, FIG. 2 is a view illustrating the detector according to the first embodiment of the present invention and illustrating a state made before a grip part 40 is coupled to the detector 100 (part (a) of FIG. 2) and a state made after the grip part 40 is coupled to the detector 100 (part (b) of FIG. 2) when viewed from above or below, FIG. 3 is a view illustrating an upper surface, a lateral surface, and a rear surface of the detector 100 according to the first embodiment of the present invention, and FIG. 4 is a transparent view illustrating the inside of the detector 100 according to the first embodiment of the present invention.

In FIGS. 1 to 4, an X-axis direction indicates a first direction (longitudinal direction), a Y-axis direction indicates a second direction (horizontal direction) perpendicular to the first direction, and a Z-axis direction indicates a vertical direction (thickness direction) perpendicular to both the first and second directions.

In addition, an X-Y plane configured by an X-axis and a Y-axis may mean a horizontal plane.

With reference to FIGS. 1 to 4, the detector 100 according to the first embodiment of the present invention includes a first part 10, a second part 20, and a reinforcement member 30. The detector 100 may refer to a device configured to obtain image information by converting light (visible light), which is emitted from a fluorescent material (e.g., a scintillator), into electric signals (electric charges) in response to radiation (X-rays, gamma rays, etc.) that penetrate the test target. However, the detector 100 is not limited thereto. The detector 100 may be a detector using a direct conversion method that converts incident radiation directly into electrical signals without a separate fluorescent material.

The first part 10 may include a first housing 12 and a detection panel 14 provided in the first housing 12.

The first housing 12 may be made of a radiolucent material and made of an elastic material that is changeable in shape. For example, the first housing 12 may be made of rubber, urethane, silicone, carbon composite materials, plastic, or the like that may transmit radiation and be changeable in shape.

The detection panel 14 may be made of a flexible material. For example, the detection panel 14 may be a flexible thin film transistor (TFT) panel and obtain image information by converting light, which is emitted from the fluorescent material, into electric signals (electric charges) in response to radiation that penetrate the test target.

The second part 20 includes a second housing 22 connected to the first part 10 (specifically, the first housing 12).

The second housing 22 may be made of an inelastic material or a material having higher rigidity than the material of the first housing 12. For example, the second housing 22 may be made of a metallic material such as aluminum, stainless steel, and magnesium, an inelastic carbon composite material, or a synthetic resin made of a secure material. In this case, the second housing 22 may accommodate therein a control part 24 to be described below and protect the control part 24 from an external impact.

For example, in case that the second housing 22 is made of a metallic material, the second housing 22 may protect the control part 24 or the like, which cannot be changed in shape, from an external impact and block noise generated in the control part 24 or introduced from the outside. In addition, the second housing 22 may be made of plastic containing fiberglass.

In the first embodiment of the present invention, the second housing 22 does not change in shape. However, the present invention is not limited thereto. Like the first housing 12, the second housing 22 may be made of an elastic material changeable in shape. In addition, in the embodiment, the second housing 22 may be made of a material higher in strength than the material of the first housing 12 so that the second housing 22 is less deformed than the first housing 12.

The reinforcement member 30 may be disposed outside the detection panel 14 and formed to surround a part of the detection panel 14 on the horizontal plane. That is, the reinforcement member 30 may be provided outside an end of the panel 14 while surrounding the detection panel 14. In the embodiment of the present invention, the reinforcement member 30 may be disposed to overlap the detection panel 14. However, with this arrangement, the reinforcement member 30 may affect an image created by the detection panel 14. Therefore, the reinforcement member 30 may be disposed outside the detection panel 14.

In the embodiment, the reinforcement member 30 may be disposed in the first housing 12 and provided in the X-axis direction at two opposite sides of the detection panel 14. In addition, one end of the reinforcement member 30 may be fixed to the second housing 22, such that the reinforcement member 30 may be disposed over the first housing 12 and the second housing 22.

The reinforcement member 30 may have a harder material than the first housing 12. For example, the reinforcement member 30 may be configured by a spring steel sheet or a metal plate or made of rubber, urethane, silicone, carbon composite materials, plastic, and the like harder than the material of the first housing 12.

Figure 5:
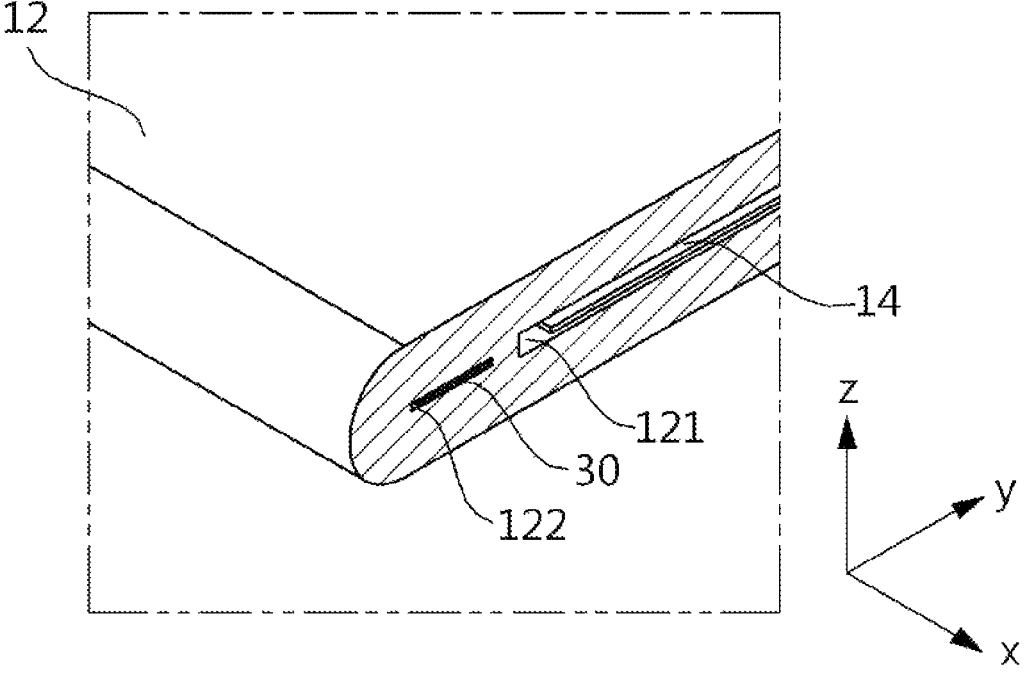
FIG. 5 is a view illustrating a cross-section of the detector according to the first embodiment of the present invention.

FIG. 5 is a view illustrating a cross-section of the detector 100 according to the first embodiment of the present invention (a cross-section taken along line A-A' in FIG. 1).

With reference to FIGS. 4 and 5, the first housing 12 includes a panel accommodation portion 121 and a reinforcement member accommodation portion 122.

The detection panel 14 may be accommodated in the panel accommodation portion 121. For example, the detection panel 14 may be inserted into the panel accommodation portion 121.

The reinforcement member accommodation portion 122 may be formed outside the panel accommodation portion 121 when viewed on the horizontal plane (the X-Y plane). The reinforcement member 30 may be accommodated in the reinforcement member accommodation portion 122. For example, the reinforcement member 30 may be accommodated in the reinforcement member accommodation portion 122 and formed by insert-injection molding, or the reinforcement member 30 may be inserted into the reinforcement member accommodation portion 122.

As illustrated in FIGS. 4 and 5, the reinforcement member accommodation portion 122 may be formed to be spaced apart from the panel accommodation portion 121 when viewed on the horizontal plane. However, the present invention is not limited thereto.

The reinforcement member accommodation portion 122 may be connected to a fixing hole 123 formed at one end of the first housing 12 based on the first direction.

In addition, a hole portion 32 may be formed at one end of the reinforcement member 30 based on the first direction and provided in the reinforcement member accommodation portion 122 so as to surround the fixing hole 123.

With reference to part (b) of FIG. 2 and FIG. 3, the grip part 40 may be provided at the other end of the second housing 22 based on the first direction that is opposite to one end of the second housing 22 based on the first direction at which the first housing 12 and the second housing 22 are connected. The grip part 40 may be coupled to grip part coupling part 26 formed at the other end of the second housing 22 based on the first direction.

In this case, one end of a fixing part 200 to be described below may be coupled to the grip part 40, and the other end of the fixing part 200 may be coupled to the fixing hole 123.

With reference to FIG. 4, the reinforcement member 30 includes connection portions 34 coupled to the inside of the second housing 22.

The second part 20 further includes the control part 24 disposed in the second housing 22 and connected to the detection panel 14. For example, the control part 24 may include components such as a printed board assembly (PBA) or a battery that does not change in shape.

As described above, the reinforcement member 30 is disposed outside the detection panel 14 and formed to surround a part of the detection panel 14 on the horizontal plane. The reinforcement member 30 may be formed to surround a part of the detection panel 14 on the horizontal plane, except for a portion where the detection panel 14 and the control part 24 are connected.

The detector 100 according to the first embodiment of the present invention may include the reinforcement member 30 formed to surround a part of the detection panel 14 disposed in the first housing 12, the reinforcement member 30 being disposed over the first housing 12 and the second housing 22, in addition to the first part 10 including the first housing 12 (elastic housing) made of a variable elastic material, and the second part 20 including the second housing 22 (inelastic housing) made of an inelastic material or a material having higher rigidity than the material of the first housing 12.

With the above-mentioned configuration, in case that the first part 10 is tightly attached to the test target and changes in shape, as described below, a high tensile force is applied to the first housing 12 and the detection panel 14 to prevent damage to the first housing 12 and the detection panel 14.

In addition, in case that the first part 10 changes in shape, the first part 10 may be prevented from being rapidly bent or folded by an external impact. In case that a radiographic inspection is not performed, the first part 10 may be immediately unfolded.

With reference to FIG. 4, the detection panel 14 includes a readout part 142 coupled to one end of the detection panel 14 based on the first direction and connected to the control part 24, and a gate part 144 coupled to a lateral portion of the detection panel 14 and connected to the control part 24.

For example, the readout part 142 may be a readout IC (ROIC) sensor provided in the form of a chip-on-film (COF), and the gate part 144 may also be provided in the form of a chip-on-film (COF). In addition, the readout part 142 and the gate part 144 may be made of a flexible material or configured as a flexible structure.

In the embodiment of the present invention, the reinforcement member 30 may be formed to surround a part of the detection panel 14 on the horizontal plane, except for the portion where the detection panel 14 and the control part 24 are connected. However, the present invention is not limited thereto. The reinforcement member 30 may be formed to surround the entire detection panel 14 on the horizontal plane.

Specifically, in case that the reinforcement member 30 is formed to surround the entire detection panel 14 on the horizontal plane, the readout part 142 may be disposed on an upper or lower portion of the reinforcement member 30 and connect the detection panel 14 and the control part 24.

With reference to FIGS. 1 to 4, the second part 20 further includes interface parts 28 formed on lateral surfaces of the second housing 22 and formed at the other end of the second housing 22 based on the first direction that is opposite to one end of the second housing 22 based on the first direction at which the first housing 12 and the second housing 22 are connected.

The interface parts 28 include a first interface part 282 formed at the other end of the second housing 22 based on the first direction, and second interface parts 284 formed on lateral surfaces of the second housing 22.

For example, the first interface part 282 may include a button or the like, and the second interface part 284 may include a communication part such as an antenna. In this case, the first interface part 282 may perform functions for a user's manipulation convenience, and the second interface part 284 may perform functions for data transmission with the detector 100 and a detector external device (a display or the like).

Figure 6:
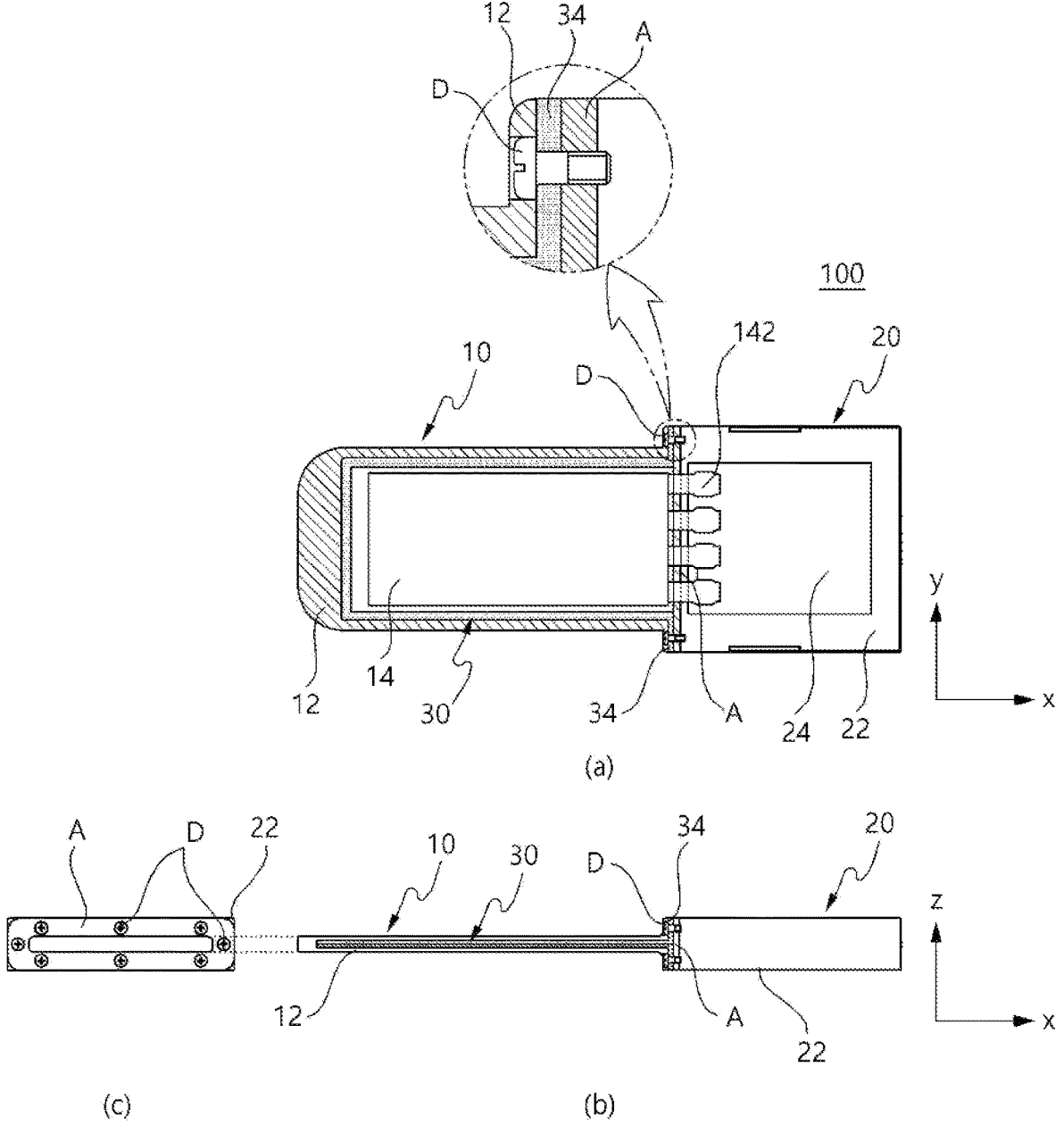
FIG. 6 is a view illustrating another embodiment of a reinforcement member provided in the detector according to the first embodiment of the present invention.

FIG. 6 is a view illustrating another embodiment of the reinforcement member 30 provided in the detector 100 according to the first embodiment of the present invention.

Specifically, part (a) of FIG. 6 is a transparent view illustrating the inside of the detector 100 when viewed from above, part (b) of FIG. 6 is a transparent view illustrating the inside of the detector 100 when viewed from the lateral side, and part (c) of FIG. 6 in FIG. 6 is a view illustrating a coupling part A and fixing members D.

In this case, in FIG. 6, the components illustrated in FIGS. 1 to 5, except for the components such as the first housing 12, the detection panel 14, the second housing 22, and the reinforcement member 30, will be omitted or illustrated as briefly as possible.

With reference to FIG. 6, unlike the embodiment illustrated in FIGS. 1 to 5, the reinforcement member 30 does not necessarily need to be disposed over the first housing 12 and the second housing 22, and the reinforcement member 30 may be coupled to an outer portion of the second housing 22.

Specifically, the reinforcement member 30 includes the connection portions 34 coupled to one end of the second housing 22 at which the first housing 12 and the second housing 22 are connected.

With reference to FIG. 6, the coupling part A may be disposed between the connection portion 34 and the second housing 22. The connection portions 34 and the coupling part A may be coupled to one end of the second housing 22 by means of the fixing members D (e.g., screws). In this case, the connection portion 34 may reinforce the coupling part A.

As illustrated in FIG. 6, the connection portion 34 may protrude in the vertical direction, but the present invention is not limited thereto. The connection portion 34 may be coupled to one end of the second housing 22 on the same horizontal plane as the detection panel 14.

As illustrated in FIG. 6, the readout part 142 may be disposed on a lower portion (or an upper portion) of the connection portion 34 protruding in the vertical direction, and the readout part 142 may pass through a hole formed at a center of the coupling part A and connect the detection panel 14 and the control part 24.

Meanwhile, in the embodiment of the present invention, the reinforcement member 30 may be disposed over the first housing 12 and the second housing 22 or disposed only in the first housing 12 without being coupled to the outer portion of the second housing 22.

Figure 7:
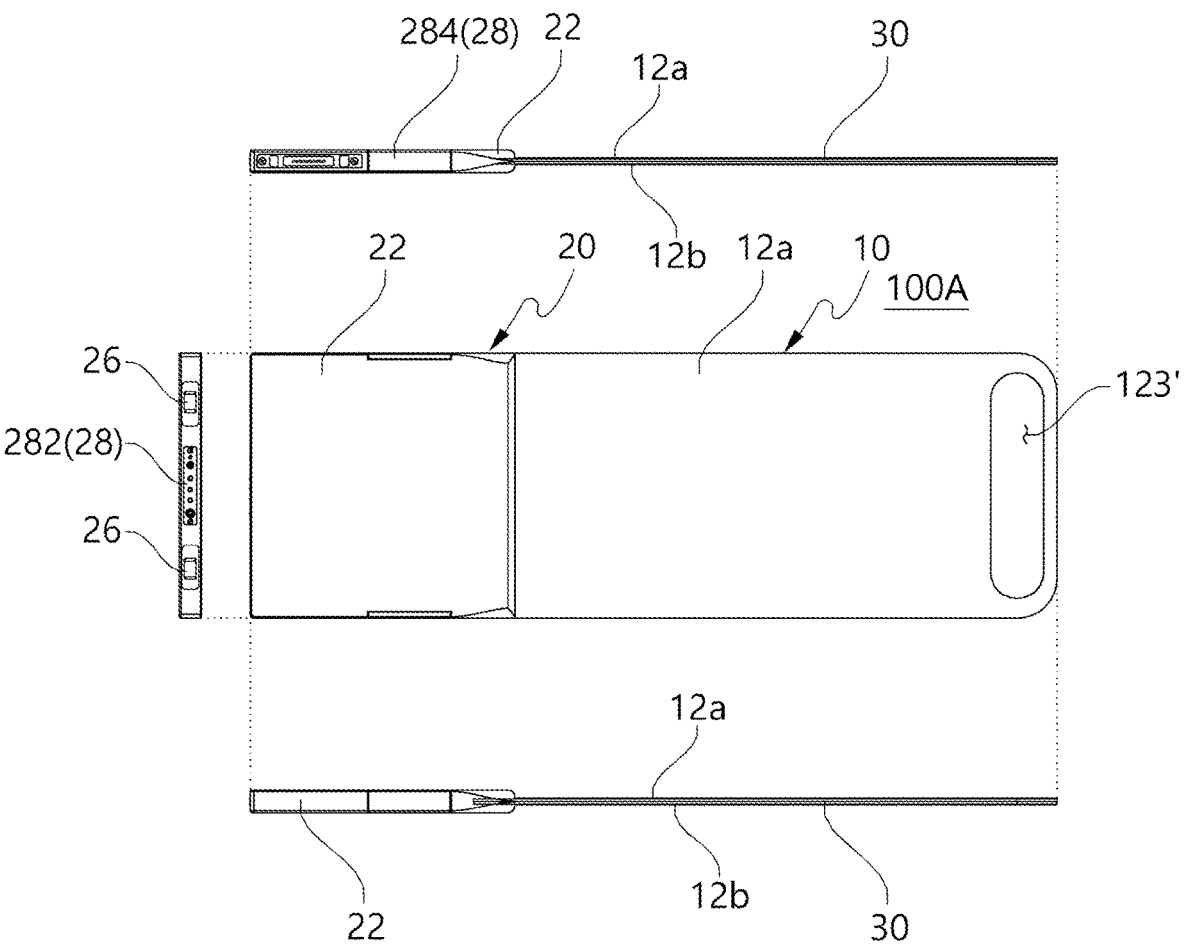
FIG. 7 is a view illustrating an upper surface, a lateral surface, and a rear surface of a detector according to a second embodiment of the present invention.
Figure 8:
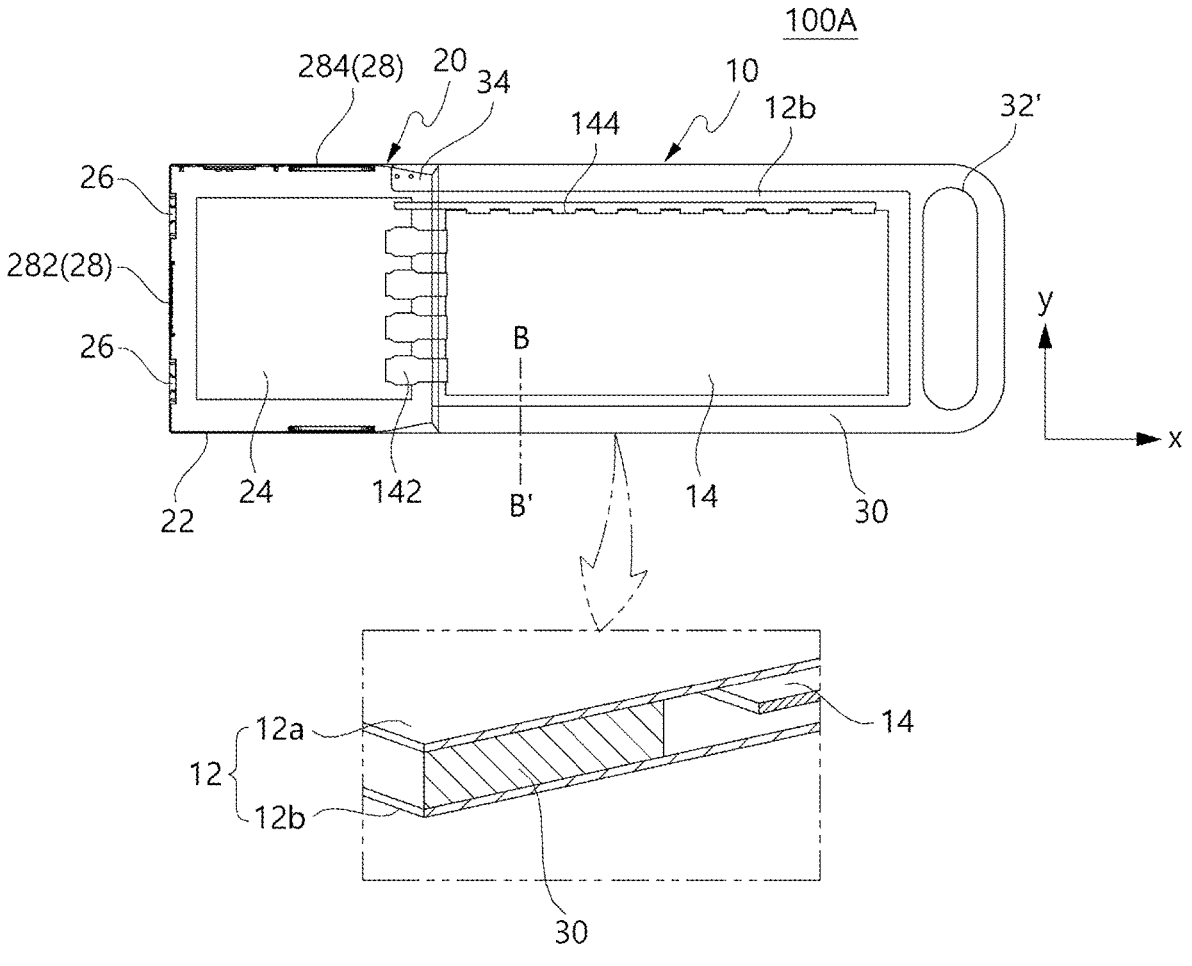
FIG. 8 is a transparent view illustrating the inside of the detector according to the second embodiment of the present invention.

FIG. 7 is a view illustrating an upper surface, a lateral surface, and a rear surface of a detector 100A according to a second embodiment of the present invention, and FIG. 8 is a transparent view illustrating the inside of the detector 100A according to the second embodiment of the present invention.

The detector 100A according to the second embodiment of the present invention does not greatly differ in configuration from the detector 100 illustrated in FIGS. 1 to 6, except that the first housing 12 is not integrated, but the first housing 12 configured by stacking an upper plate (first plate 12a), a lower plate (second plate 12b), and a sidewall (the reinforcement member 30) configured to connect the upper plate and the lower plate, unlike the detector 100 illustrated in FIGS. 1 to 6. Therefore, in the embodiment of the detector 100A described with reference to FIGS. 7 and 8, a detailed description of the components identical to the components of the detector 100 illustrated in FIGS. 1 to 6 will be omitted, and only the difference will be described in detail.

In the detector 100A, the first housing 12 includes the first plate 12a disposed on one surface of the reinforcement member 30 (the upper surface of the reinforcement member 30), and the second plate 12b disposed on the other surface of the reinforcement member 30 (the lower surface of the reinforcement member 30) opposite to one surface of the reinforcement member 30 in the vertical direction. In this case, as illustrated in FIG. 8, the reinforcement member 30 may define the sidewall of the first housing 12, but the present invention is not limited thereto. The first plate 12a or the second plate 12b may be disposed to cover the lateral surface of the reinforcement member 30.

For example, the first plate 12a and the second plate 12b may be made of the same material as the integrated first housing 12 of the detector 100 according to the first embodiment.

A hole portion 32' may be formed at one end of the reinforcement member 30 of the detector 100A according to the second embodiment. A fixing hole 123' may be formed in surfaces of the first and second plates 12a and 12b that are in contact with the hole portion 32', and the fixing hole 123' may correspond in shape to the hole portion 32' in the vertical direction.

In the detector 100 according to the first embodiment, the hole portion 32 is formed to surround the fixing hole 123 in the reinforcement member accommodation portion 122 formed in the integrated first housing 12. In contrast, in the detector 100A according to the second embodiment, the first housing 12 is not integrated, but the first housing 12 may be configured by stacking the first and second plates 12a and 12b, at the upper and lower portions, and the reinforcement member 30, i.e., the sidewall that connects the first plate 12a and the second plate 12b.

Therefore, the fixing hole 123' of the detector 100A may be formed in a shape corresponding to the shape of the hole portion 32' formed on the reinforcement member 30, but the present invention is not limited thereto. The fixing hole 123' may be formed to be smaller than the hole portion 32' formed on the reinforcement member 30.

In addition, in the case of the detector 100A according to the second embodiment, the other end of the fixing part 200 may be coupled to the hole portion 32' to be described below.

Figure 9:
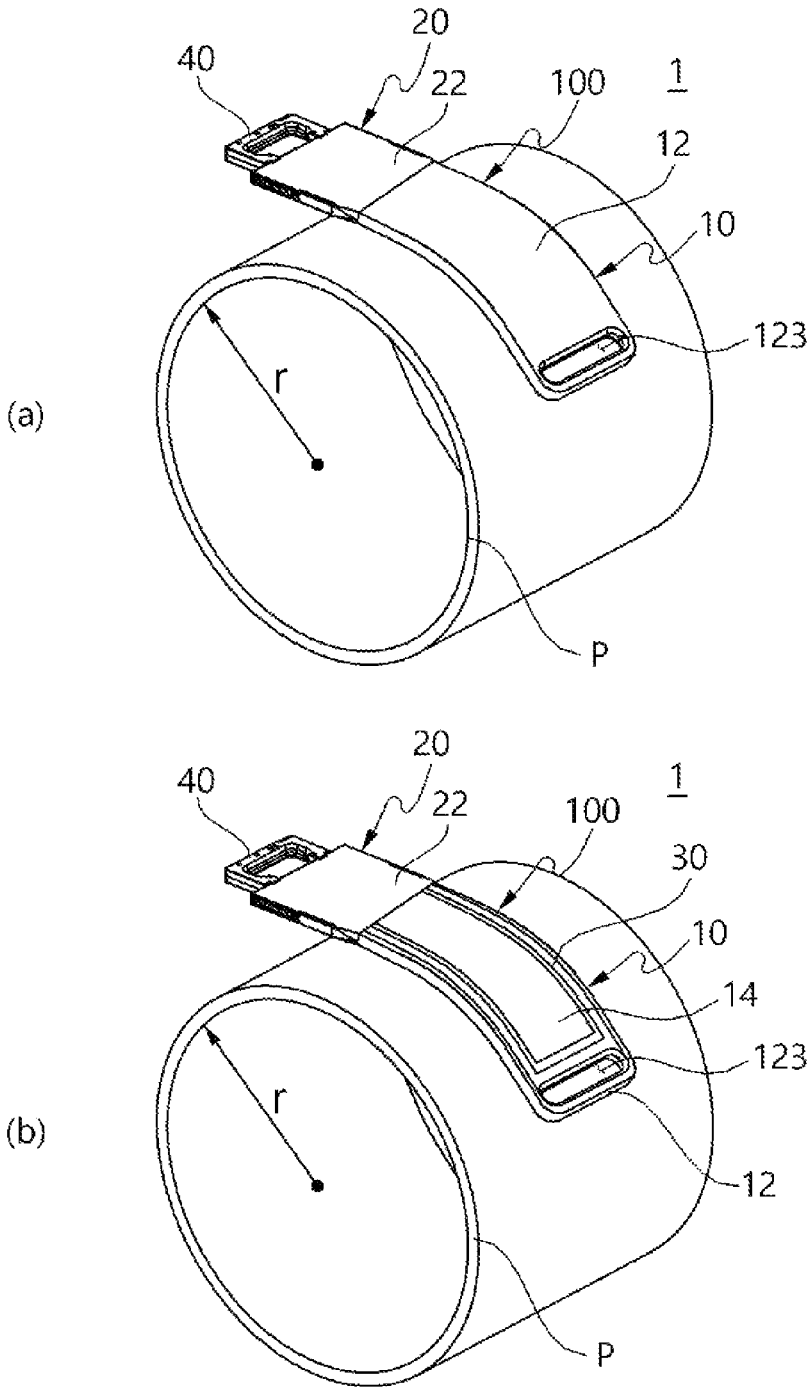
FIG. 9 is a perspective view of an imaging device including the detector according to the present invention.
Figure 10:
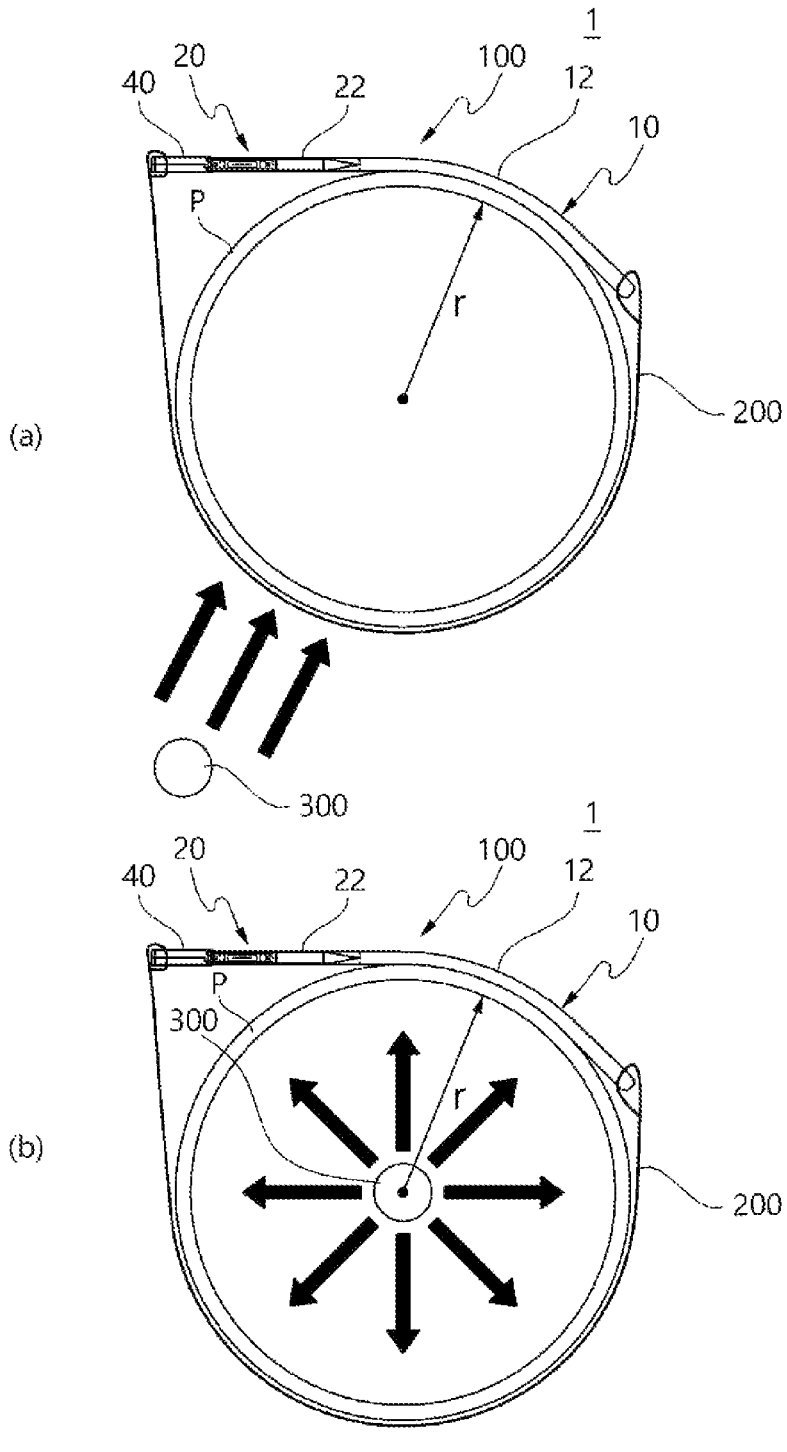
FIG. 10 is a view illustrating the imaging device including the detector according to the present invention when viewed from the lateral side.

FIG. 9 is a perspective view of an imaging device 1 including the detector 100 according to the present invention, and FIG. 10 is a view illustrating the imaging device 1 including the detector 100 according to the present invention when viewed from the lateral side.

In this case, part (a) of FIG. 9 is a view illustrating an external appearance of the imaging device 1, part (a) of FIG. 9 is a transparent view illustrating the first part 10 of the detector 100 in the imaging device 1, part (a) of FIG. 10 is a view illustrating a state in which a radioactive ray generation part 300 is disposed outside a test target P, and part (b) of FIG. 10 is a view illustrating a state in which the radioactive ray generation part 300 is disposed inside the test target P.

Meanwhile, in FIG. 9, the fixing part 200 and the radioactive ray generation part 300 are not illustrated.

In addition, FIGS. 9 and 10 illustrate the detector 100 having the integrated first housing 12 illustrated in FIGS. 1 to 6. However, the detector 100 illustrated in FIGS. 9 and 10 may be the detector 100A with a stacked structure instead of the integrated structure illustrated in FIGS. 7 and 8.

In FIGS. 9 and 10, an r direction means a radial direction of the test target P. The radiation emitted from the radioactive ray generation part 300 may penetrate the test target P and reach the detector 100. In this case, the test target P may be a welded structure such as a pipe. However, the present invention is not limited thereto. Any structure may be applied as a test target as long as the structure has a curved surface.

With reference to FIGS. 9 and 10, the imaging device 1 includes the detector 100, the fixing part 200, and the radioactive ray generation part 300.

With reference to FIG. 10, one end of the fixing part 200 may be coupled to the grip part 40 of the detector 100, and the other end of the fixing part 200 may be coupled to the fixing hole 123 of the detector 100 or coupled to the reinforcement member 30 provided on the detector 100, such that the detector 100 may be tightly fixed to the test target P. For example, the fixing part 200 may be configured as a band, a strip, a wire, a belt, a ratchet belt, an iron chain, a Velcro fastener, and the like.

Specifically, in case that the detector 100 has the integrated first housing 12, as illustrated in FIGS. 1 to 6, the other end of the fixing part 200 may be coupled to the fixing hole 123 of the detector 100.

In contrast, as illustrated in FIGS. 7 and 8, in case that the detector 100 has the stacked first housing 12, the other end of the fixing part 200 may pass through the fixing hole 123' and be coupled to the hole portion 32' of the reinforcement member 30.

As illustrated in part (a) of FIG. 10, the radioactive ray generation part 300 may be disposed outside the test target P. As illustrated in part (b) of FIG. 10, the radioactive ray generation part 300 may be disposed inside the test target P.

As illustrated in FIGS. 9 and 10, in the detector 100, the first part 10 made of an elastic material may be tightly attached to the test target P, such that the shape of the first part 10 may be changed to a curved shape. However, the second part 20, which is made of an inelastic material or a material having higher rigidity than the material of the first housing 12, may not change in shape.

As illustrated in FIGS. 9 and 10, the detector 100 is tightly attached to the test target P. Therefore, in case that the first part 10 changes in shape, the reinforcement member 30 may prevent the first part 10 from being rapidly bent or folded by an external impact. In case that a radiographic inspection is not performed, the reinforcement member 30 may immediately unfold the first part 10.

Figure 11:
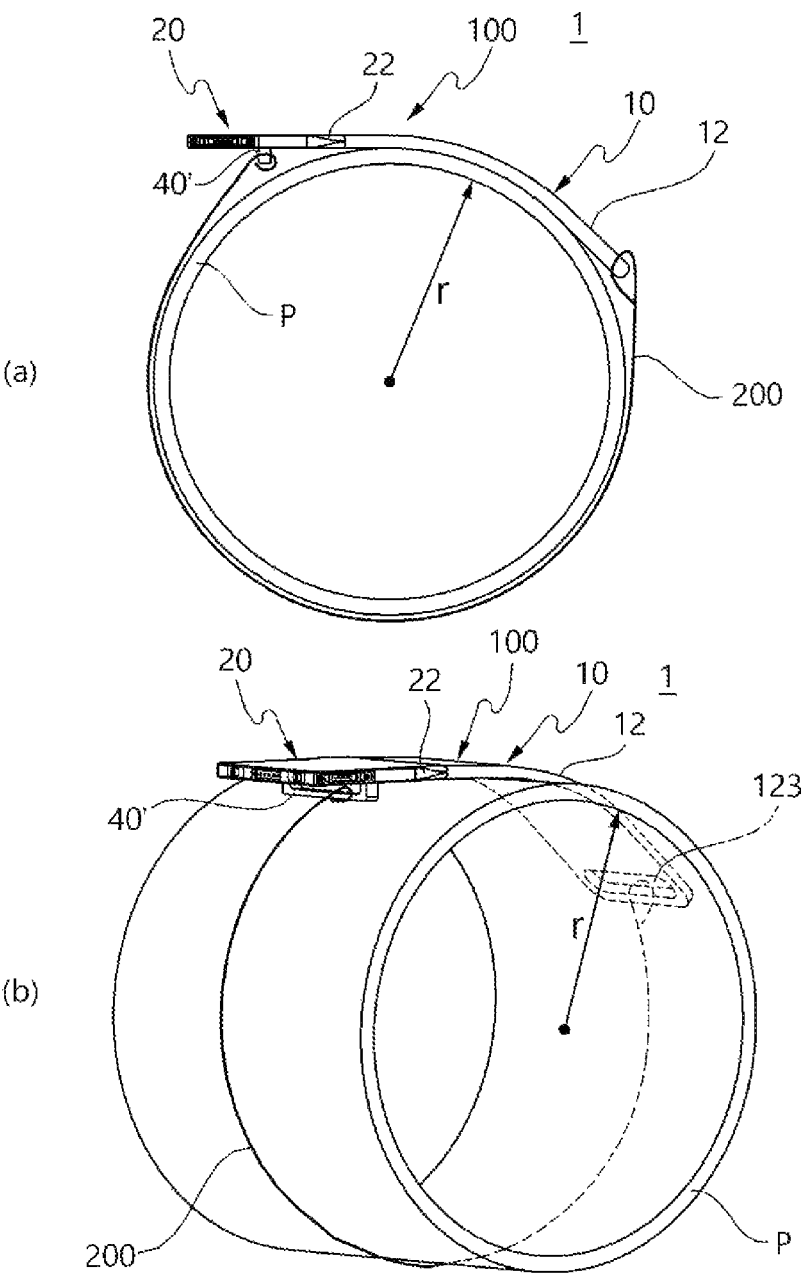
FIG. 11 is a view illustrating another embodiment of a grip part of the detector according to the present invention.

FIG. 11 is a view illustrating another embodiment of the grip part 40' of the detector 100 according to the present invention. In this case, part (a) of FIG. 11 is a view illustrating the imaging device 1 when viewed from the lateral side, and part (b) of FIG. 11 is a transparent view illustrating the test target P of the imaging device 1.

Meanwhile, in FIG. 11, the radioactive ray generation part 300 is not illustrated.

In addition, FIG. 11 illustrates the detector 100 having the integrated first housing 12 illustrated in FIGS. 1 to 6. However, the detector 100 illustrated in FIG. 11 may be the detector 100 with the stacked structure illustrated in FIGS. 7 and 8.

In FIG. 11, the grip part 40' provided in the detector 100 may be formed on the rear surface of the second housing 22. Although not illustrated, in case that the grip part 40' is formed on the rear surface of the second housing 22, the grip part coupling part 26, to which the grip part 40' is coupled, may be formed on the rear surface of the second housing 22.

In the case of the embodiment illustrated in FIG. 11, one end of the fixing part 200 is coupled to the grip part 40' formed on the rear surface of the second housing 22, and the other end of the fixing part 200 may be coupled to the fixing hole 123 of the detector 100 or coupled to the reinforcement member 30 provided on the detector 100, such that the detector 100 may be tightly fixed to the test target P.

In the embodiment of the present invention, one end of the fixing part 200 does not necessarily need to be coupled to the grip part 40 or 40' but may be coupled to a separate connection component (not illustrated, e.g., a hook or the like) provided on the second housing 22.

In addition, in FIGS. 10 and 11, the fixing part 200 coupled to the grip part 40 or 40' may be disposed to be close to the first housing 12 made of an elastic material, such that the first housing 12 may be attached to the test target P as tightly as possible. For example, one end of the fixing part 200 may be coupled to the grip part 40 or 40' or the separate connection component so that one end and the other end of the fixing part 200 based on the first direction of the first housing 12 may be disposed as close as possible to the test target P.

Figure 12:
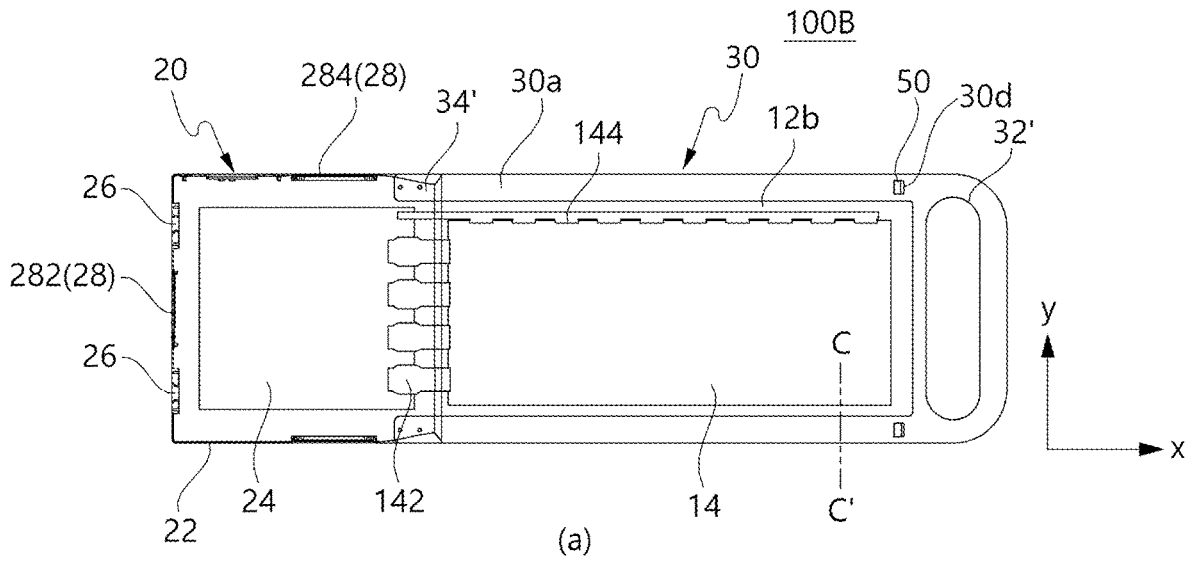
FIG. 12 is a transparent view illustrating the inside of a detector according to a third embodiment of the present invention.
Figure 12:
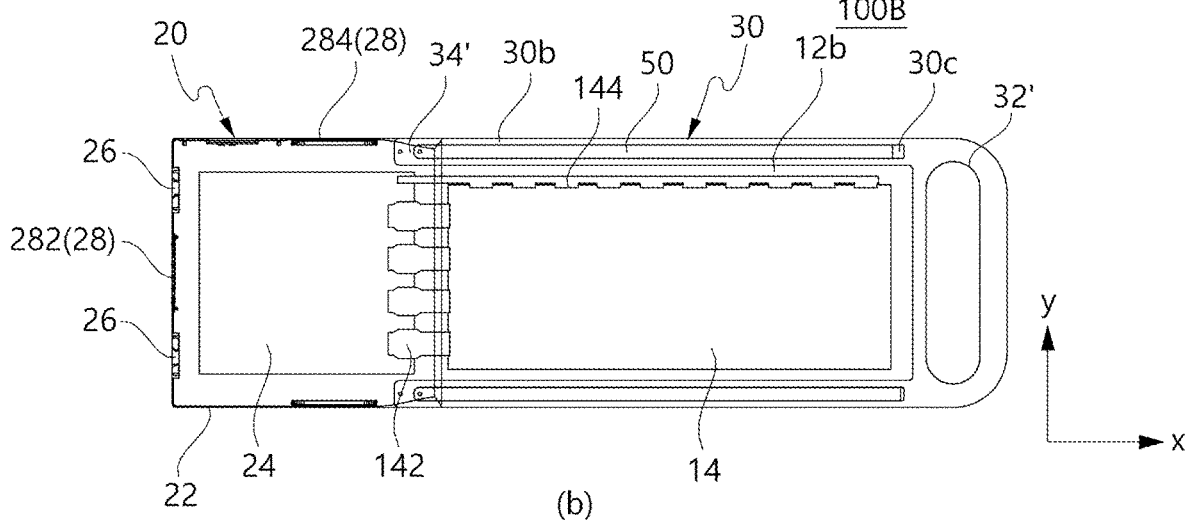
Figure 13:
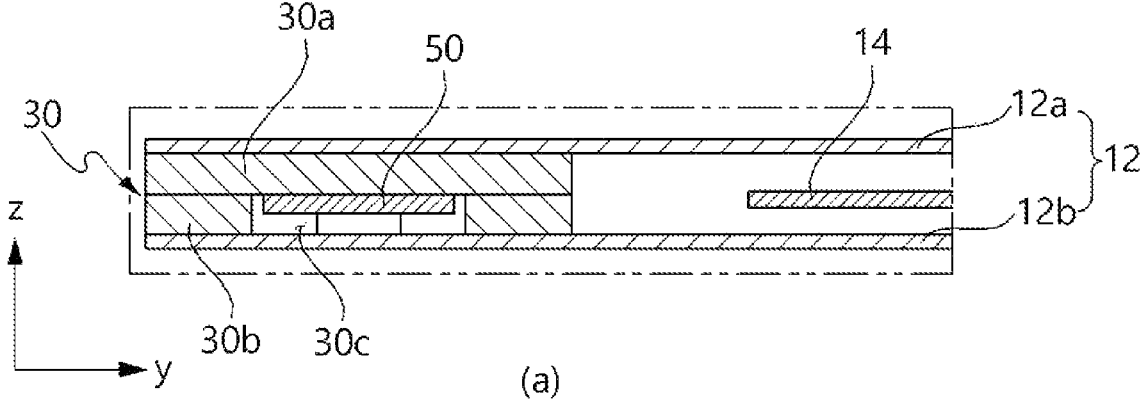
FIG. 13 is a view illustrating a cross-section of the detector according to the third embodiment of the present invention.
Figure 13:
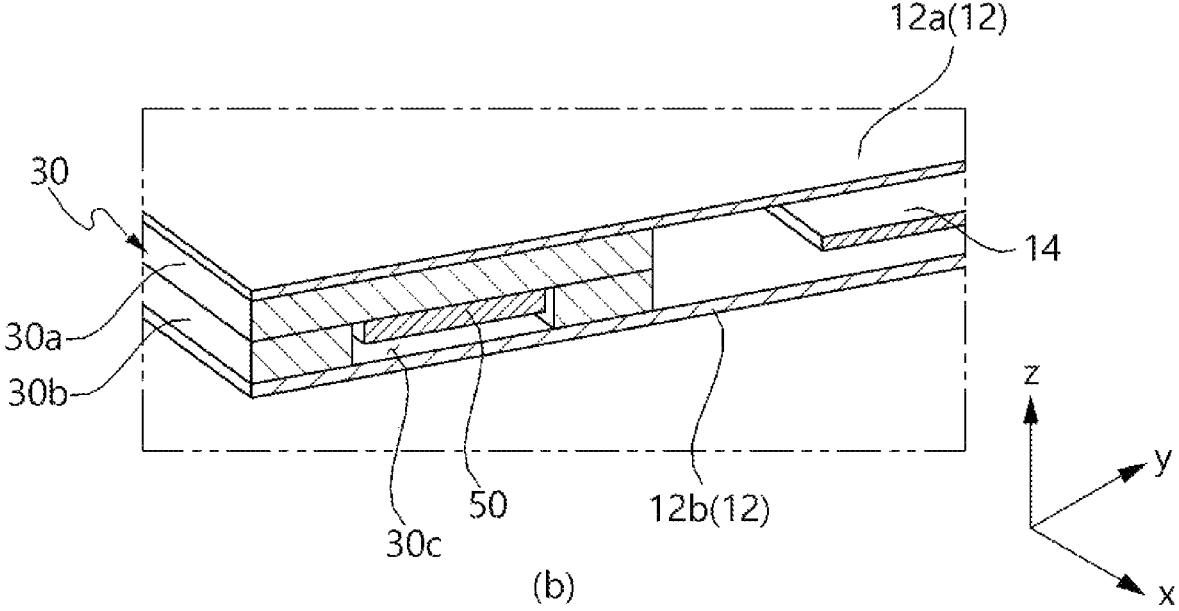
Figure 14:
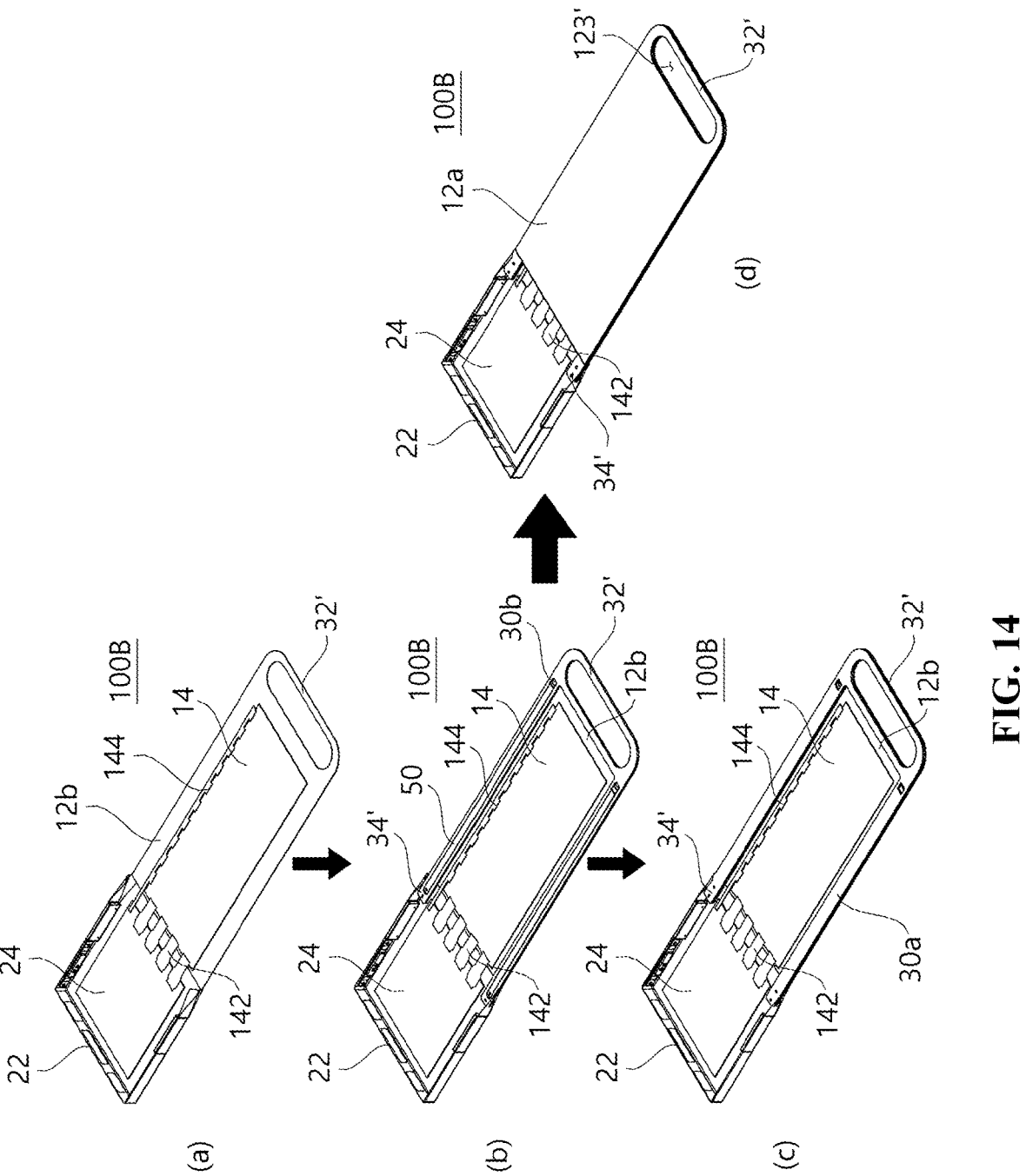
FIG. 14 is a view illustrating a part of a process of manufacturing the detector according to the third embodiment of the present invention.

FIG. 12 is a transparent view illustrating the inside of the detector 100B according to the third embodiment of the present invention, FIG. 13 is a view illustrating a cross-section (cross-sectional view taken along line C-C' in FIG. 12) of a detector 100B according to a third embodiment of the present invention, and FIG. 14 is a view illustrating a part of a process of manufacturing the detector 100B according to the third embodiment of the present invention. In this case, part (a) of FIG. 12 is a view illustrating a state in which a first reinforcement plate 30a of the reinforcement member 30 is disposed in the detector 100B, part (b) of FIG. 12 is a view illustrating a state made before the first reinforcement plate 30a of the reinforcement member 30 is disposed in the detector 100B, part (a) of FIG. 13 is a view illustrating a cross-section on a Y-Z plane of the detector 100B, and part (b) of FIG. 13 is a view obliquely illustrating a cross-section of the detector 100B.

The detector 100B according to the third embodiment of the present invention does not greatly differ in configuration from the detector 100A illustrated in FIGS. 7 and 8, except that the reinforcement member 30 is divided into the first reinforcement plate 30a and the second reinforcement plate 30b without being integrated, and bending restriction parts 50 are provided on the reinforcement member 30 (specifically, a second reinforcement plate 30b) and configured to restrict a degree to which the first part 10 is maximally bendable.

Therefore, regarding the detector 100B according to the third embodiment, a detailed description of the components identical to the components of the detector 100A illustrated in FIGS. 7 and 8 will be omitted, and only the difference will be described in detail. In addition, in the case of the detector 100B according to the third embodiment, the first housing 12 is described as having a stacked structure, like the detector 100A according to the second embodiment. However, the present invention is not limited thereto. Like the detector 100 illustrated in FIGS. 1 to 6, the first housing 12 may be integrated.

With reference to FIGS. 12 and 13, in the detector 100B of the third embodiment, the reinforcement member 30 includes the first reinforcement plate 30a having one surface (the upper surface of the first reinforcement plate 30a) on which the first plate 12a is disposed, and the second reinforcement plate 30b disposed on the other surface of the first reinforcement plate 30a (the lower surface of the first reinforcement plate 30a) opposite to one surface of the first reinforcement plate 30a in the vertical direction.

In addition, the second plate 12b may be disposed on the other surface of the second reinforcement plate 30b (the lower surface of the second reinforcement plate 30b) opposite, in the vertical direction, to one surface of the second reinforcement plate 30b (the upper surface of the second reinforcement plate 30b) being in contact with the other surface of the first reinforcement plate 30a.

The hole portion 32' may be formed at one end of the reinforcement member 30 of the detector 100B of the third embodiment. In this case, the hole portion 32' may be formed by stacking the first reinforcement plate 30a and the second reinforcement plate 30b in the vertical direction.

In addition, in the detector 100B of the third embodiment, the reinforcement member 30 includes connection portions 34' coupled to the inside of the second housing 22. In this case, the connection portion 34' may be formed by stacking the first reinforcement plate 30a and the second reinforcement plate 30b in the vertical direction.

With reference to FIG. 14, a part of the process of manufacturing the detector 100B of the third embodiment will be described below.

First, as illustrated in part (a) of FIG. 14, the second housing 22, in which the control part 24 is disposed, and the second plate 12b having the upper portion, on which the detection panel 14 connected to the control part 24 is disposed, may be disposed in parallel in the first direction.

Next, as illustrated in part (b) of FIG. 14, the second reinforcement plate 30b may be disposed on the upper portion of the second plate 12b, and a part of the second reinforcement plate 30b may be coupled to the inside of the second housing 22.

Next, as illustrated in part (c) of FIG. 14, the first reinforcement plate 30a may be disposed on the upper portion of the second reinforcement plate 30b, and a part of the first reinforcement plate 30a may be coupled to the inside of the second housing 22. Therefore, the reinforcement member 30 may be coupled to the inside of the second housing 22 by means of the connection portions 34'.

Finally, as illustrated in part (d) of FIG. 14, the first plate 12a may be disposed on the upper portion of the first reinforcement plate 30a.

Figure 15:
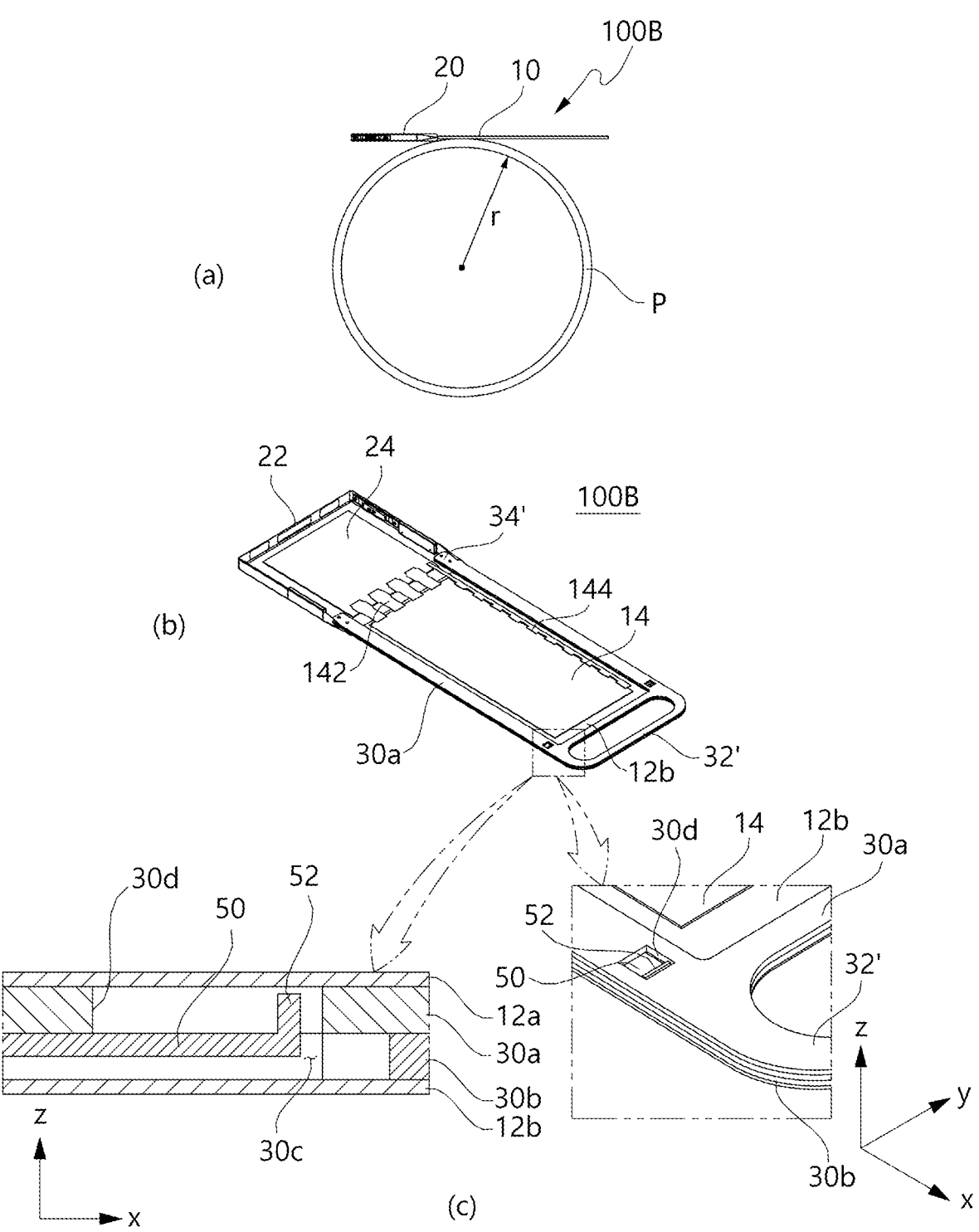
FIGS. 15 and 16 are views illustrating operating states of a bending restriction part provided in the detector according to the third embodiment of the present invention.
Figure 16:
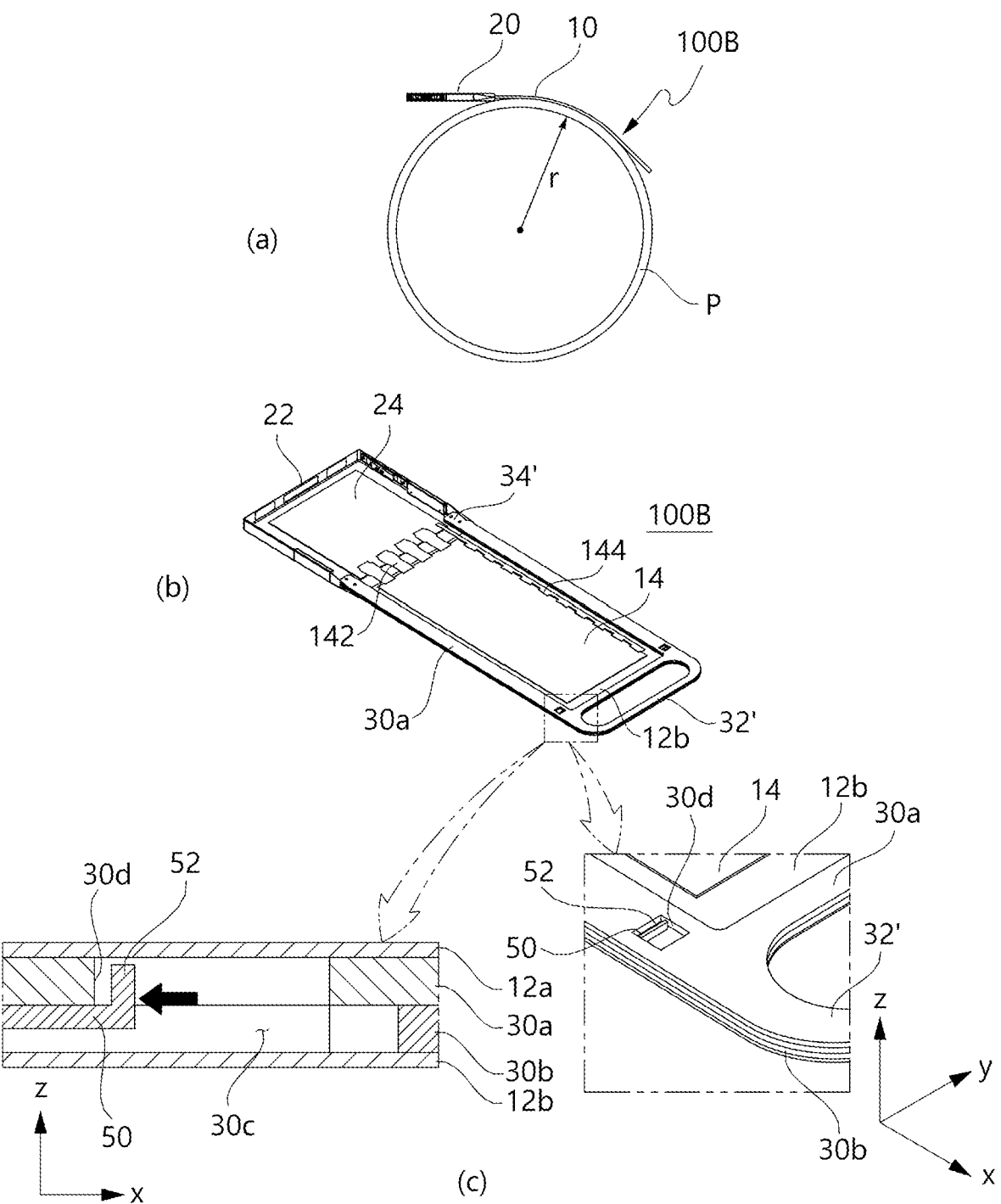

FIGS. 15 and 16 are views illustrating operating states of the bending restriction part 50 provided in the detector 100B according to the third embodiment. In this case, FIG. 15 is a view illustrating a state made before the first part 10 is tightly attached to the test target P, and FIG. 16 is a view illustrating a state in which the first part is tightly attached to the test target P and bent maximally.

With reference to FIGS. 12 to 16, the detector 100B of the third embodiment includes the bending restriction part 50 configured to restrict a degree to which the first part 10 is maximally bendable.

The bending restriction part 50 may have a harder material than the first housing 12. For example, the bending restriction part 50 may be configured by a spring steel sheet or a metal plate and made of rubber, urethane, silicone, carbon composite materials, plastic, and the like harder than the material of the first housing 12.

The bending restriction parts 50 may be disposed in bending restriction part guide portions 30c formed in the second reinforcement plate 30b and disposed in the first direction on the horizontal plane. In this case, a pair of bending restriction part guide portions 30c may be formed in the second direction with the detection panel 14 interposed therebetween. A pair of bending restriction parts 50 may also be formed in the second direction and disposed in the bending restriction part guide portions 30c with the detection panel 14 interposed therebetween. However, the present invention is not limited thereto. The number of bending restriction part guide portions 30c or the number of bending restriction parts 50 may be one, three, or more.

The bending restriction part 50 includes a protruding portion 52 protruding from one end in the vertical direction. The first reinforcement plate 30a includes a stopper portion 30d configured to come into contact with the protruding portion 52 in the first direction when the bending restriction part 50 moves in the first direction on the horizontal plane.

Although not illustrated in detail in FIGS. 12 to 16, the protruding portion 52 may protrude in the vertical direction from one end of the bending restriction part 50 so as to have a predetermined angle.

In this case, the stopper portion 30d may be disposed adjacent to the hole portion 32'.

As illustrated in FIG. 15, the bending restriction part 50 may be positioned at a side of the hole portion 32' before the first part 10 is bent. As illustrated in FIG. 16, when the first part 10 is tightly attached to the test target P and bent, the bending restriction part 50 may move in the first direction on the horizontal plane along the bending restriction part guide portion 30c.

FIG. 16 is a view illustrating a state in which the first part 10 is tightly attached to the test target P and bent maximally. The state in which the first part 10 is maximally bent may be a state in which the protruding portion 52 and the stopper portion 30d are in contact with each other.

As described above, the detector 100B of the third embodiment includes the bending restriction part 50 provided in the reinforcement member 30 and configured to restrict a degree to which the first part 10 is maximally bendable, which may prevent the first part 10 including the detection panel 14 from being infinitely deformed, thereby preventing damage to the first part 10 including the detection panel 14.

Figure 17:
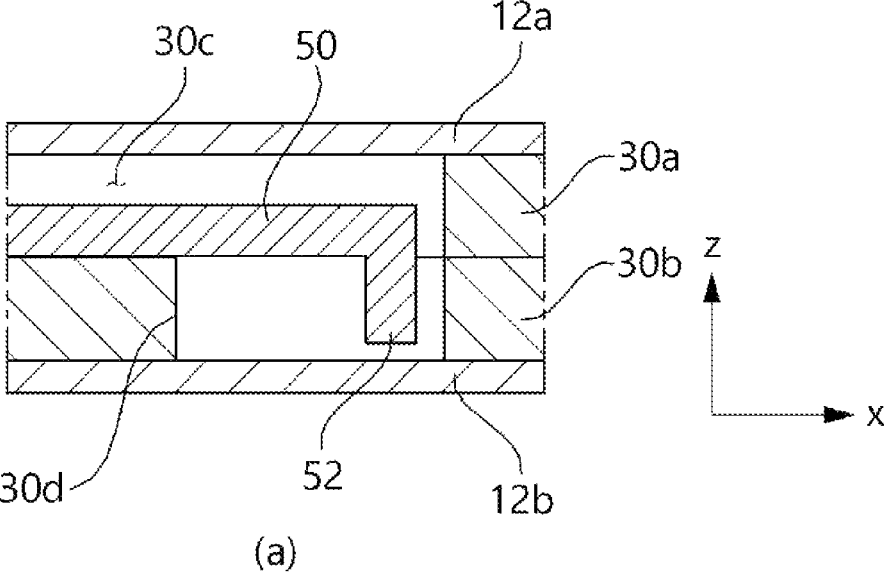
FIG. 17 is a view illustrating another embodiment of the bending restriction part provided in the detector according to the third embodiment of the present invention.
Figure 17:
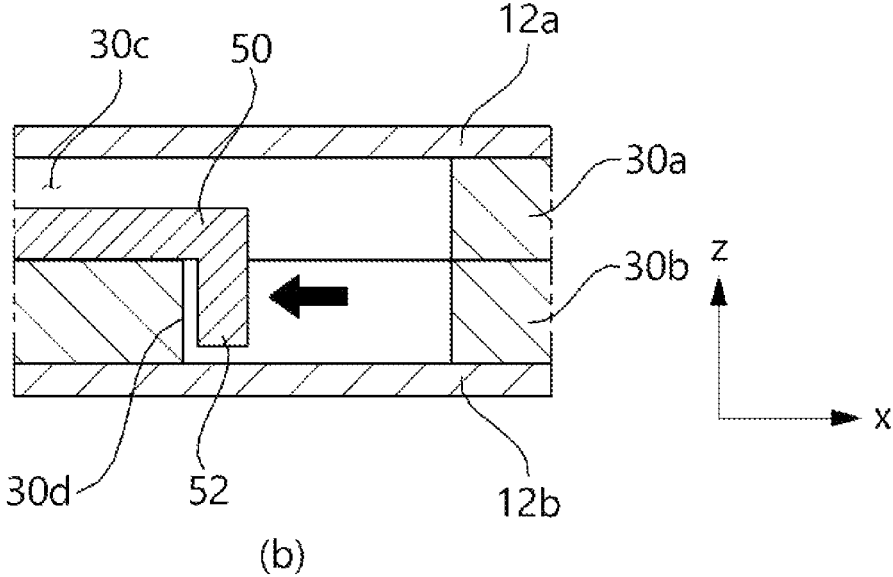

FIG. 17 is a view illustrating another embodiment of the bending restriction part 50 provided in the detector according to the third embodiment of the present invention. In this case, part (a) of FIG. 17 is a view illustrating a state made before the bending restriction part 50 is moved in the first direction (X-axis direction), and part (b) of FIG. 17 is a view illustrating a state in which the bending restriction part 50 is moved in the first direction and the protruding portion 52 of the bending restriction part 50 is in contact with the stopper portion 30d.

With reference to FIG. 17, unlike the embodiment illustrated in FIGS. 12 to 16, the bending restriction part guide portion 30c may be formed in the first reinforcement plate 30a and disposed in the first direction on the horizontal plane. The bending restriction part 50 may be disposed in the bending restriction part guide portion 30c formed in the first reinforcement plate 30a.

In this case, unlike the embodiment illustrated in FIGS. 12 to 16, the protruding portion 52 of the bending restriction part 50 may protrude downward in the vertical direction, and the stopper portion 30d may be formed on the second reinforcement plate 30b.

Although not illustrated in detail in FIG. 17, the protruding portion 52 may protrude downward in the vertical direction from one end of the bending restriction part 50 so as to have a predetermined angle.

In addition, although not illustrated in detail in FIG. 17, the stopper portion 30d may be disposed adjacent to the hole portion 32'.

As illustrated in part (a) of FIG. 17, the bending restriction part 50 may be positioned at a side of the hole portion 32' before the first part 10 is bent. As illustrated in part (b) of FIG. 17, when the first part 10 is tightly attached to the test target P and bent, the bending restriction part 50 may move in the first direction on the horizontal plane along the bending restriction part guide portion 30c. In this case, as illustrated in part (b) of FIG. 17, when the bending restriction part 50 moves in the first direction on the horizontal plane, the protruding portion 52 may come into contact with the stopper portion 30d in the first direction.

Part (b) of FIG. 17 is a view illustrating a state in which the first part 10 is tightly attached to the test target P and bent maximally. The state in which the first part 10 is maximally bent may be a state in which the protruding portion 52 and the stopper portion 30d are in contact with each other.

In the case of the embodiment illustrated in FIG. 17, because the bending restriction part 50 is disposed in the bending restriction part guide portion 30c formed in the first reinforcement plate 30a, the bending restriction part 50 may be disposed adjacent to the first plate 12a of the first housing 12. Therefore, a distance that the bending restriction part 50 moves in the first direction may be lengthened by a radius deviation occurring when the first part 10 is bent in comparison with the embodiment illustrated in FIG. 16.

Figure 18:
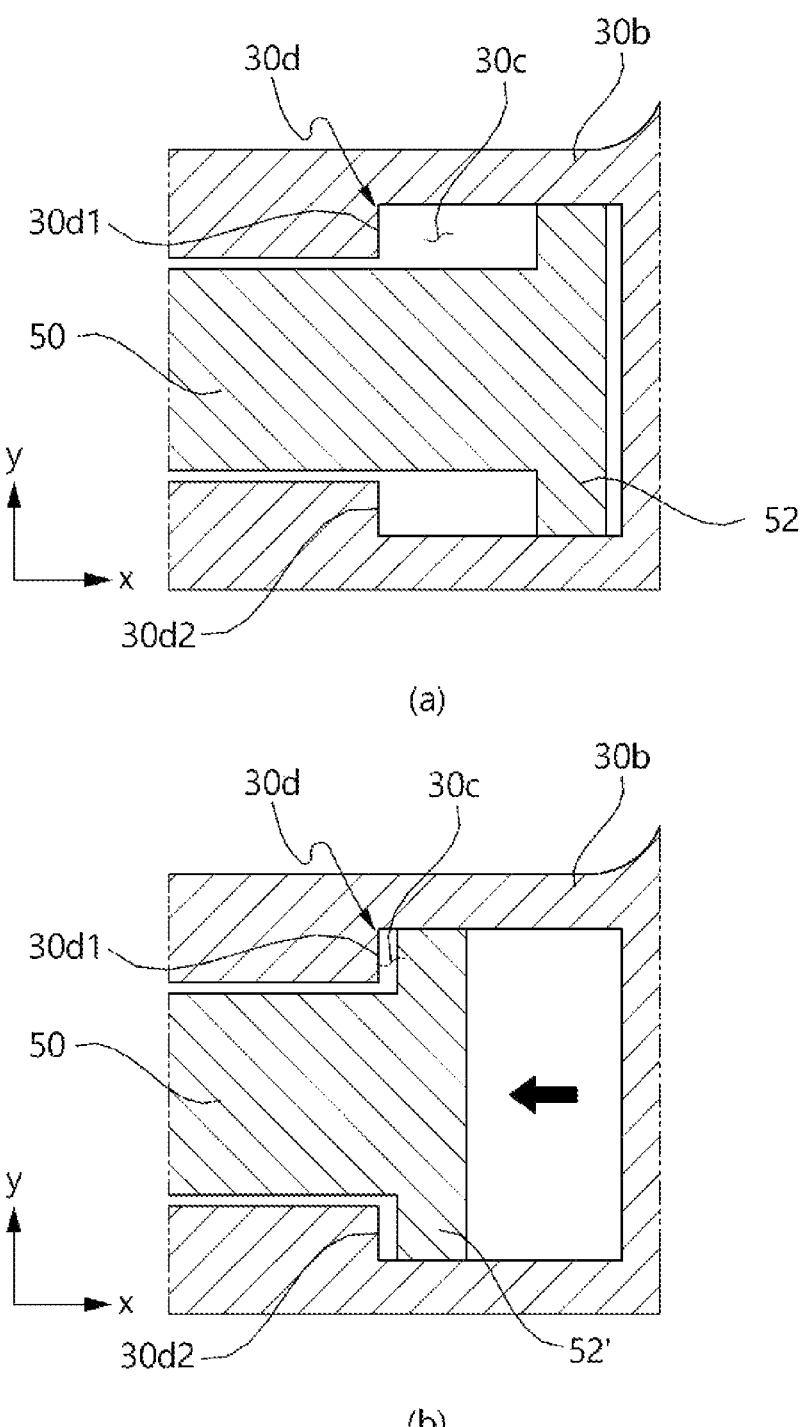
FIG. 18 is a view illustrating still another embodiment of the bending restriction part provided in the detector according to the third embodiment of the present invention.

FIG. 18 is a view illustrating still another embodiment of the bending restriction part 50 provided in the detector according to the third embodiment of the present invention. In this case, part (a) of FIG. 18 is a view illustrating a state made before the bending restriction part 50 is moved in the first direction (X-axis direction), and part (b) of FIG. 18 is a view illustrating a state in which the bending restriction part 50 is moved in the first direction and a protruding portion 52' of the bending restriction part 50 is in contact with the stopper portion 30*d*.

Unlike the bending restriction part 50 illustrated in FIGS. 12 to 17, the bending restriction part 50 illustrated in FIG. 18 includes the protruding portion 52' protruding from one end in the second direction perpendicular to the first direction, instead of the protruding portion 52 protruding from one end in the vertical direction or protruding from one end so as to have a predetermined angle with respect to the vertical direction.

Although not illustrated in detail in FIG. 18, the protruding portion 52' may protrude from one end of the bending restriction part 50 so as to have a predetermined angle with respect to the second direction.

The second reinforcement plate 30*b* includes a stopper portion 30*d* formed at one end of the bending restriction part guide portion 30*c* and including a first end 30*d*1 and a second end 30*d*2 disposed to face each other in the second direction on the horizontal plane.

In this case, as in the embodiment illustrated in FIG. 17, the bending restriction part guide portion 30*c* may be formed in the first reinforcement plate 30*a*, and the stopper portion 30*d* may also be formed on the first reinforcement plate 30*a*.

Although not illustrated in detail in FIG. 18, the stopper portion 30*d* may be disposed adjacent to the hole portion 32'.

As illustrated in part (a) of FIG. 18, the bending restriction part 50 may be positioned at a side of the hole portion 32' before the first part 10 is bent. As illustrated in part (b) of FIG. 18, when the first part 10 is tightly attached to the test target P and bent, the bending restriction part 50 may move in the first direction on the horizontal plane along the bending restriction part guide portion 30*c*. In this case, as illustrated in part (b) of FIG. 18, when the bending restriction part 50 moves in the first direction on the horizontal plane, the protruding portion 52' may come into contact with the stopper portion 30*d* in the first direction.

Part (b) of FIG. 18 is a view illustrating a state in which the first part 10 is tightly attached to the test target P and bent maximally. The state in which the first part 10 is maximally bent may be a state in which the protruding portion 52' and the stopper portion 30*d* are in contact with each other.

Figure 19:
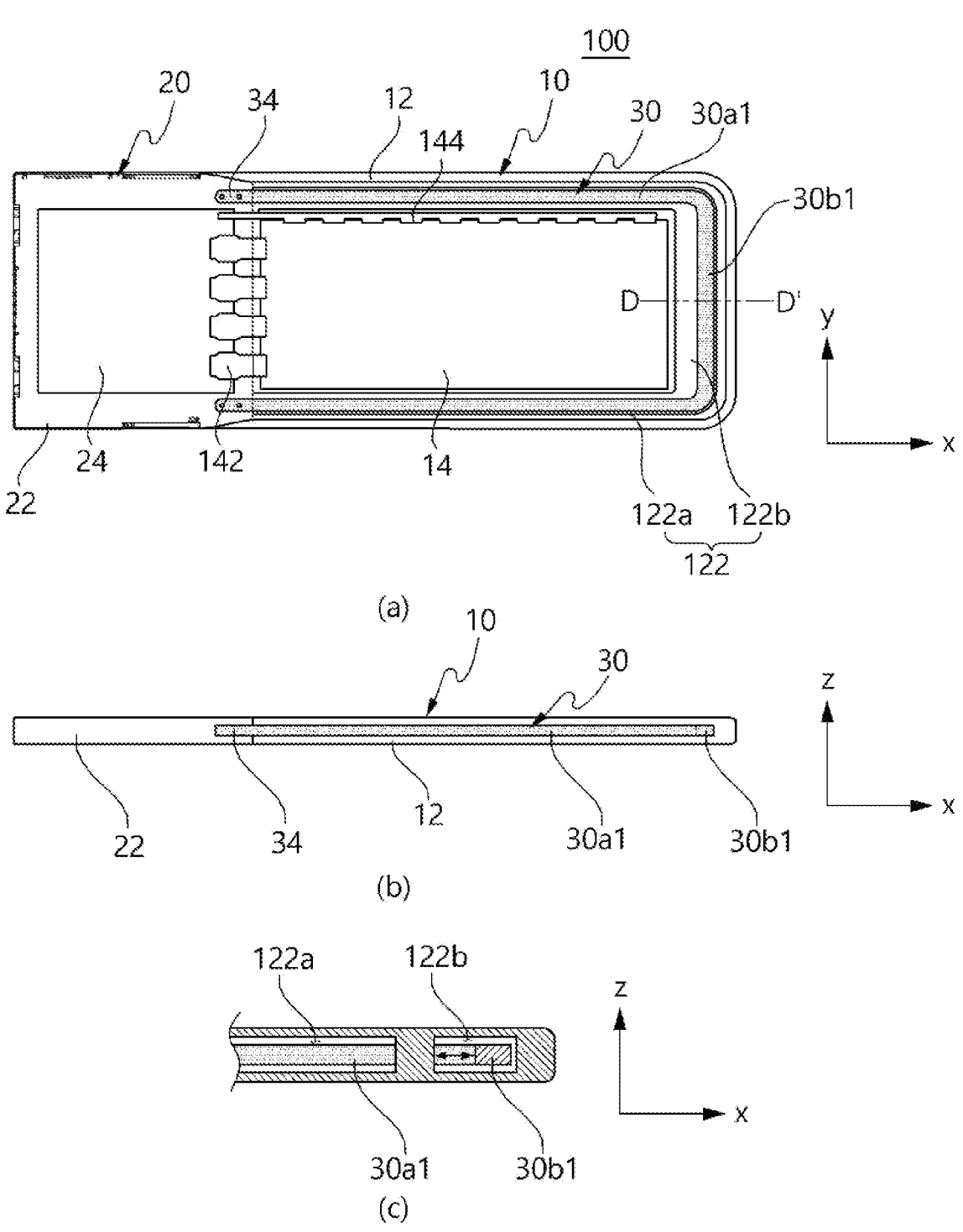
FIG. 19 is a view illustrating an embodiment in which the reinforcement member in the detector according to the first embodiment of the present invention is used to restrict a degree to which a first part is bendable.

FIG. 19 is a view illustrating an embodiment in which the reinforcement member 30 in the detector 100 according to the first embodiment of the present invention is used to restrict a degree to which the first part 10 is bendable. Specifically, part (a) of FIG. 19 is a transparent view illustrating the inside of the detector 100 according to the first embodiment when viewed from above, part (b) of FIG. 19 is a transparent view illustrating the inside of the detector 100 according to the first embodiment when viewed from the lateral side, and part (c) of FIG. 19 is a cross-sectional view taken along line D-D' of part (a) of FIG. 19.

In this case, in FIG. 19, the components illustrated in FIGS. 1 to 5, except for the components such as the first housing 12, the detection panel 14, the second housing 22, and the reinforcement member 30, will be omitted or illustrated as briefly as possible.

With reference to FIG. 19, the reinforcement member 30 includes first reinforcement portions 30*a*1 disposed in first accommodation regions 122*a* of the reinforcement member accommodation portion 122 in the first direction, and a second reinforcement portion 30*b*1 disposed in a second accommodation region 122*b* of the reinforcement member accommodation portion 122 in the second direction perpendicular to the first direction.

Specifically, in the embodiment illustrated in FIG. 19, the reinforcement member 30 may be integrated as the first reinforcement portion 30*a*1 of the reinforcement member 30 is connected to the second reinforcement portion 30*b*1 of the reinforcement member 30.

In addition, the reinforcement member accommodation portion 122 may be integrated as the first accommodation region 122*a* of the reinforcement member accommodation portion 122, which accommodates the reinforcement member 30, is connected to the second accommodation region 122*b* of the reinforcement member accommodation portion 122. In this case, the first accommodation region 122*a* may be formed in the first direction, and the second accommodation region 122*b* may be formed in the second direction.

In addition, a pair of first accommodation regions 122*a* may be formed in the second direction with the detection panel 14 interposed therebetween. A pair of first reinforcement portions 30*a*1 of the reinforcement member 30 may also be formed in the second direction and disposed in the first accommodation regions 122*a* with the detection panel 14 interposed therebetween. However, the present invention is not limited thereto. The number of first accommodation regions 122*a* or the number of first reinforcement portions 30*a*1 may be one.

Unlike the embodiment illustrated in FIGS. 12 to 18, in the embodiment illustrated in FIG. 19, the reinforcement member 30 may restrict a degree to which the first part 10 is maximally bendable. As described above, the reinforcement member 30 may have a harder material than the first housing 12.

In the embodiment illustrated in FIG. 19, the first reinforcement portion 30*a*1 and the second reinforcement portion 30*b*1 of the reinforcement member 30 are connected and integrated, and the connection portions 34 of the reinforcement member 30 are fixedly coupled to the second housing 22, such that the movement in the second direction of the reinforcement member 30 may be restricted, and the degree to which the first part 10 is maximally bendable may be restricted only in the first direction.

In the embodiment illustrated in FIG. 19, the second reinforcement portion 30*b*1 of the reinforcement member 30 may be disposed in the second accommodation region 122*b* and spaced apart from an inner wall of the second accommodation region 122*b* based on the first direction at a predetermined interval. Therefore, the second reinforcement portion 30*b*1 of the reinforcement member 30 may move in the first direction in the second accommodation region 122*b* on the horizontal plane.

Although not illustrated in detail in FIG. 19, the second reinforcement portion 30*b*1 of the reinforcement member 30 may be disposed adjacent to the fixing hole 123. For example, the reinforcement member 30 may be formed to surround the fixing hole 123 on the horizontal plane (the embodiment illustrated in FIG. 19) and formed to surround only the detection panel 14 on the horizontal plane without surrounding the fixing hole 123.

In the embodiment illustrated in FIG. 19, before the first part 10 is bent, the second reinforcement portion 30*b*1 is positioned at one end of the first housing 12 based on the first direction opposite to the fixing hole 123 adjacent to the detection panel 14. When the first part 10 is tightly attached to the test target P and bent, the second reinforcement portion 30*b*1 may be moved in the first direction (the direction of the second housing 22) on the horizontal plane. The state in which the first part 10 is maximally bent may be the state in which the second reinforcement portion 30*b*1 is in contact with the inner wall of the second accommodation region 122*b* based on the first direction.

As described above, in the detector 100 illustrated in FIG. 19, the reinforcement member 30 is configured as the bending restriction part that restricts the degree to which the first part 10 is maximally bendable. Unlike the embodiment illustrated in FIGS. 12 to 18, it is possible to prevent infinite deformation of the first part 10 including the detection panel 14 without configuring a separate bending restriction part, thereby preventing damage to the first part 10 including the detection panel 14.

Figure 20:
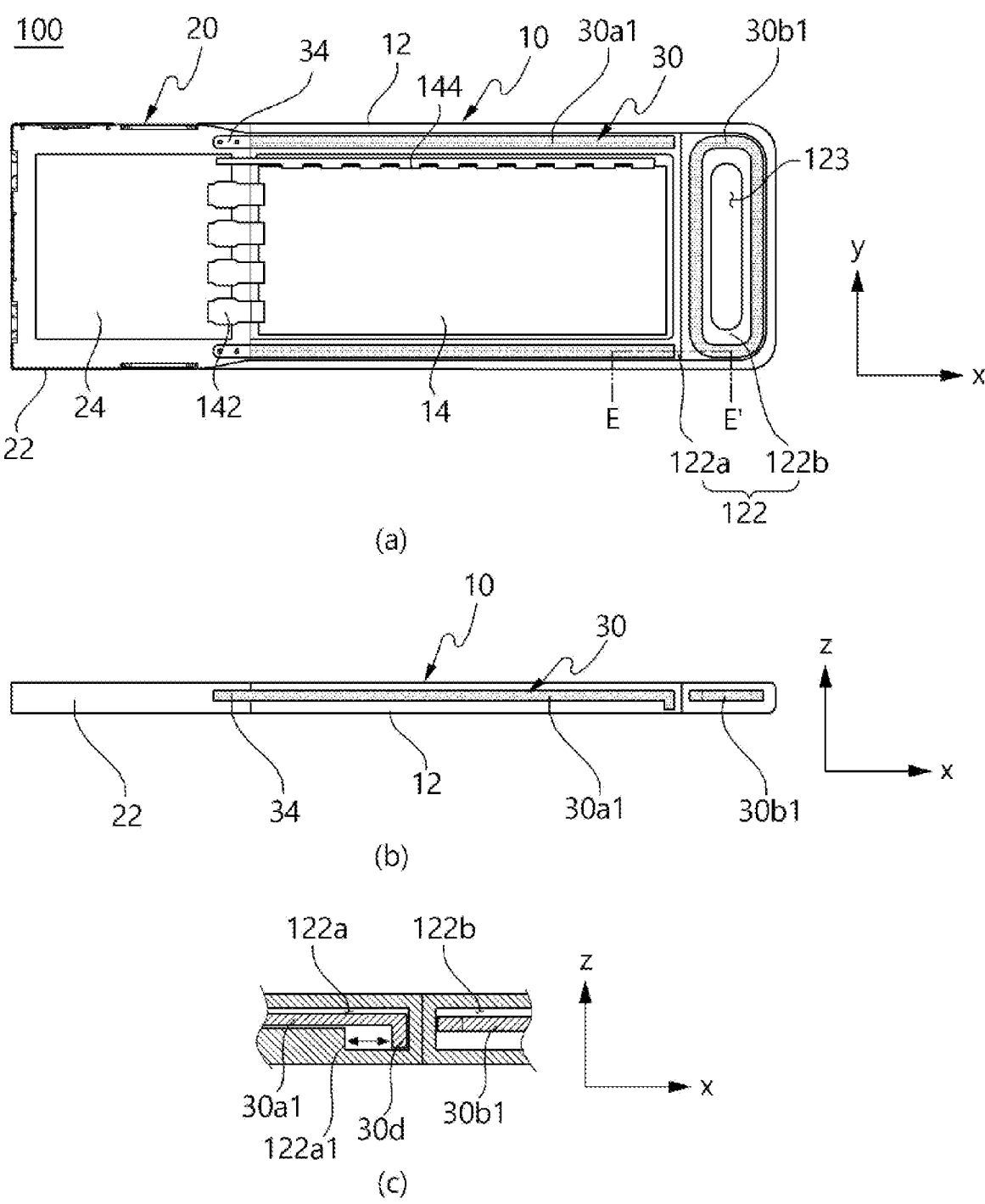
FIG. 20 is a view illustrating another embodiment in which the reinforcement member in the detector according to the first embodiment of the present invention is used to restrict a degree to which the first part is bendable.

FIG. 20 is a view illustrating another embodiment in which the reinforcement member 30 in the detector 100 according to the first embodiment of the present invention is used to restrict the degree to which the first part 10 is bendable. Specifically, part (a) of FIG. 20 is a transparent view illustrating the inside of the detector 100 according to the first embodiment when viewed from above, part (b) of FIG. 20 is a transparent view illustrating the inside of the detector 100 according to the first embodiment when viewed from the lateral side, and part (c) of FIG. 20 is a cross-sectional view taken along line E-E' of part (a) of FIG. 20.

In this case, in FIG. 20, the components illustrated in FIGS. 1 to 5, except for the components such as the first housing 12, the detection panel 14, the second housing 22, and the reinforcement member 30, will be omitted or illustrated as briefly as possible.

With reference to FIG. 20, the reinforcement member 30 includes the first reinforcement portions 30*a*1 disposed in the first accommodation regions 122*a* of the reinforcement member accommodation portion 122 in the first direction, and the second reinforcement portion 30*b*1 disposed in the second accommodation region 122*b* of the reinforcement member accommodation portion 122 in the second direction perpendicular to the first direction.

Specifically, unlike the embodiment illustrated in FIG. 19, in the embodiment illustrated in FIG. 20, the first reinforcement portion 30*a*1 of the reinforcement member 30 may be formed to be separated from the second reinforcement portion 30*b*1 of the reinforcement member 30 in the first direction.

In addition, the first accommodation region 122*a* of the reinforcement member accommodation portion 122, which accommodates the reinforcement member 30, may be formed to be separated from the second accommodation region 122*b* of the reinforcement member accommodation portion 122 in the first direction. In this case, the first accommodation region 122*a* may be formed in the first direction, and the second accommodation region 122*b* may be formed in the second direction.

In addition, a pair of first accommodation regions 122*a* may be formed in the second direction with the detection panel 14 interposed therebetween. A pair of first reinforcement portions 30*a*1 of the reinforcement member 30 may also be formed in the second direction and disposed in the first accommodation regions 122*a* with the detection panel 14 interposed therebetween. However, the present invention is not limited thereto. The number of first accommodation regions 122*a* or the number of first reinforcement portions 30*a*1 may be one.

Unlike the embodiment illustrated in FIG. 19, in the embodiment illustrated in FIG. 20, the reinforcement member 30 is formed such that the first reinforcement portion 30*a*1, which is disposed in the first direction, and the second reinforcement portion 30*b*1, which is disposed in the second direction, are separated from each other, the reinforcement member 30 may restrict the degree to which the first part 10 is maximally bendable in both the first and second directions.

In the embodiment illustrated in FIG. 20, the first reinforcement portion 30*a*1 of the reinforcement member 30 includes a protruding portion 30*d* protruding from one end in the vertical direction. The first accommodation region 122*a* includes a stopper portion 122*a*1 configured to come into contact with the protruding portion 30*d* in the first direction when the first reinforcement portion 30*a*1 moves in the first direction on the horizontal plane.

Although not illustrated in detail in FIG. 20, the protruding portion 30*d* may protrude from one end of the first reinforcement portion 30*a*1 so as to have a predetermined angle with respect to the vertical direction. In addition, although not illustrated in FIG. 19, even in the embodiment illustrated in FIG. 19, the protruding portion 30*d* may be formed at one end of the first reinforcement portion 30*a*1, like the embodiment illustrated in FIG. 20.

In addition, in the embodiment illustrated in FIG. 20, the second reinforcement portion 30*b*1 of the reinforcement member 30 may be disposed in the second accommodation region 122*b* and completely tightly attached to or almost tightly attached to the inner wall of the second accommodation region 122*b* based on the first direction, and the second reinforcement portion 30*b*1 of the reinforcement member 30 may be disposed to be spaced apart from the inner wall of the second accommodation region 122*b* based on the second direction at a predetermined interval. Therefore, the second reinforcement portion 30*b*1 of the reinforcement member 30 may move in the second direction in the second accommodation region 122*b* on the horizontal plane.

However, like the embodiment illustrated in FIG. 19, in the embodiment illustrated in FIG. 20, the second reinforcement portion 30*b*1 may be disposed in the second accommodation region 122*b* and spaced apart from the inner wall of the second accommodation region 122*b* based on the first direction at a predetermined interval, and the second reinforcement portion 30*b*1 may move in the second accommodation region 122*b* in the first direction on the horizontal plane.

As illustrated in FIG. 20, the second reinforcement portion 30*b*1 of the reinforcement member 30 may be formed in the second accommodation region 122*b* and surround the fixing hole 123.

In the embodiment illustrated in FIG. 20, the first reinforcement portion 30*a*1 is positioned at a side of the fixing hole 123 before the first part 10 is bent. When the first part 10 is tightly attached to the test target P and bent, the first reinforcement portion 30*a*1 may move in the first direction (the direction of the second housing 22) on the horizontal plane. The state in which the first part 10 is maximally bent in the first direction may be the state in which the protruding portion 30*d* and the stopper portion 122*a*1 are in contact with each other.

In addition, in the embodiment illustrated in FIG. 20, when the first part 10 is tightly attached to the test target P and bent, the second reinforcement portion 30*b*1 may move in the second direction on the horizontal plane. The state in which the first part 10 is maximally bent in the second direction may be the state in which the second reinforcement portion 30*b*1 is in contact with the inner wall of the second accommodation region 122*b* based on the second direction.

Figure 21:
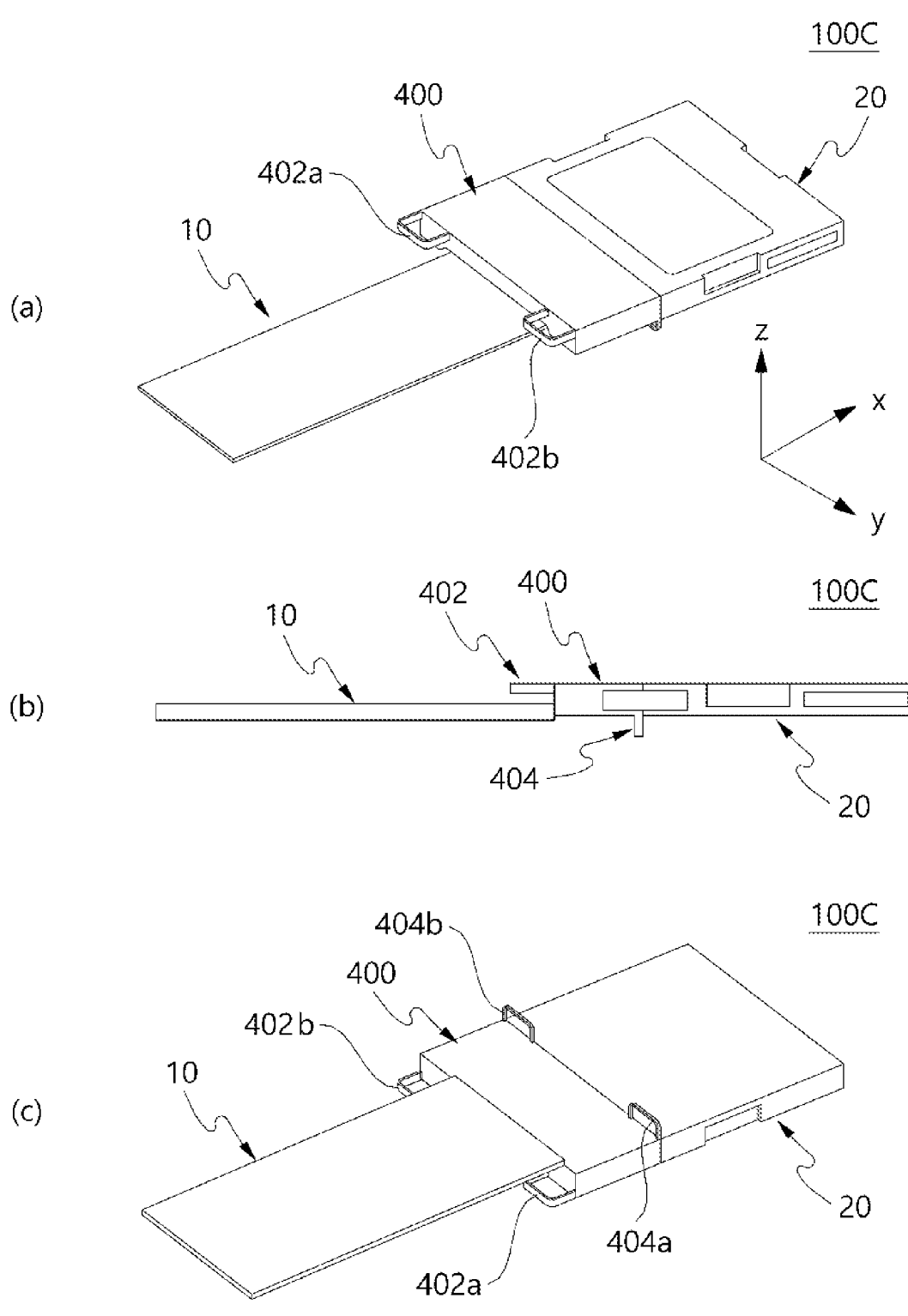
FIG. 21 is a view illustrating a detector according to a fourth embodiment of the present invention.
Figure 22:
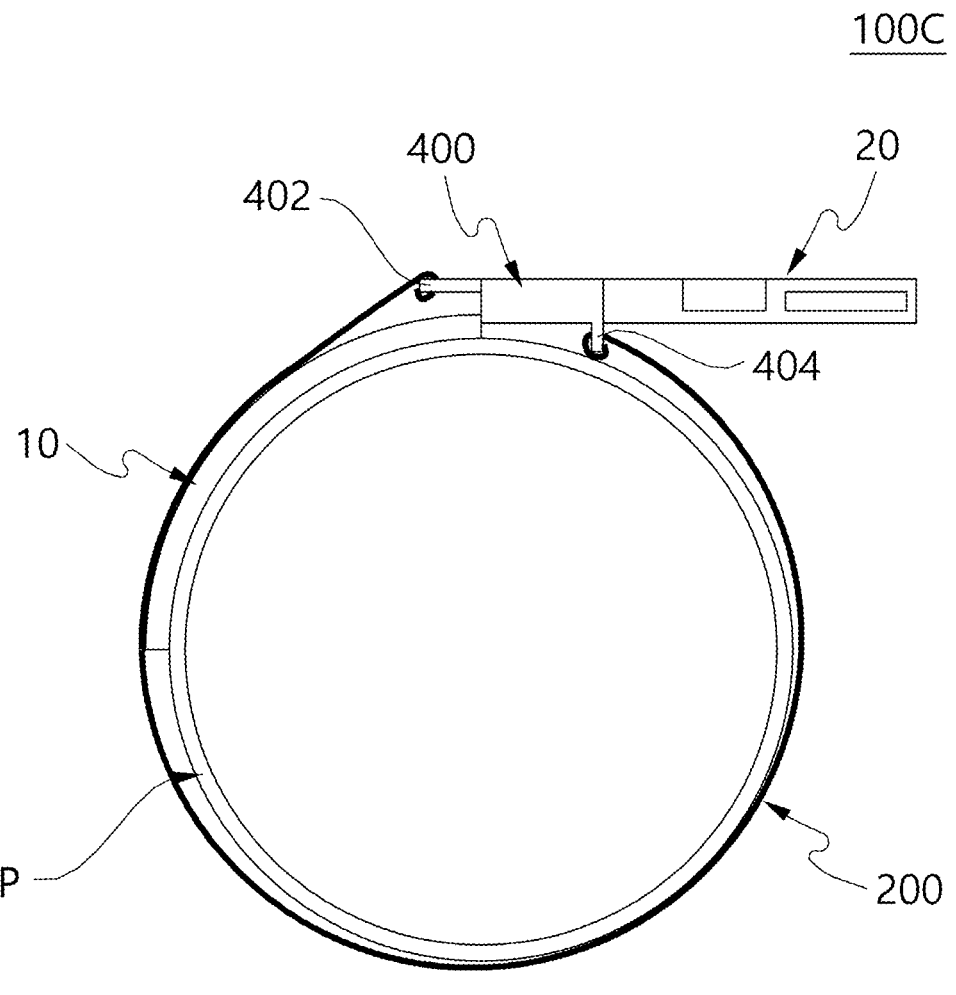
FIG. 22 is a view illustrating a state in which the detector according to the fourth embodiment of the present invention is mounted on a test target.

FIG. 21 is a view illustrating a detector according to a fourth embodiment of the present invention, and FIG. 22 is a view illustrating a state in which the detector according to the fourth embodiment of the present invention is mounted on the test target.

Part (a), part (b) and part (c) of FIG. 21 are a perspective view, a side view, and a rear perspective view of a detector 100C, respectively, according to the fourth embodiment of the present invention.

The detector 100C according to the fourth embodiment of the present invention includes the first part 10 and the second part 20 and further includes a fixing block 400 configured to fix the detector 100C to the test target. Because the detector 100C according to the fourth embodiment may adopt the basic configurations of the detectors 100, 100A, and 100B according to the first to third embodiments, the description will be focused on a difference.

The fixing block 400 includes a first ring portion 402 formed in the first direction, and a second ring portion 404 formed in the second direction different from the first direction. In the embodiment, the first direction may be the X-axis direction, i.e., the extension direction of the first part 10 with respect to the second part 20, and the second direction may be the Z-axis direction, i.e., the downward direction of the fixing block 400.

In the embodiment, the first ring portion 402 may be provided on the fixing block 400 and disposed above the first part in the Z-axis direction. In addition, the second ring portion 402 may be formed at a bottom side of the fixing block 400.

In the embodiment in FIG. 21, the fixing block 400 is illustrated as being provided on the second part 20. However, the second housing 22, which constitutes the second part 20, may serve as the fixing block 400. That is, the first ring portion 402 and the second ring portion 404 may be formed on the second part 20.

In the embodiment, the first ring portion 402 may be provided as at least two first ring portions 402a and 402b disposed in the Y-axis direction, and the second ring portion 404 may be provided as at least two second ring portions 404a and 404b disposed in the Y-axis direction.

With reference to FIG. 22, one end of the fixing part 200 may be fixed to the first ring portion 402, and the other end of the fixing part 200 may be fixed to the second ring portion 404, such that the first part 10 may be tightly attached to the test target P. The first part 10 may be effectively tightly attached to the test target P in the directions in which the first ring portion 402 and the second ring portion 404 are formed.

In the embodiment, the first ring portions 402a and 402b and the second ring portions 404a and 404b may be formed in the outward direction of the detection panel 14 to prevent the fixing part 200, which connects the first ring portions 402a and 402b and the second ring portions 404a and 404b, from applying pressure directly to the detection panel 14 provided on the first part 10. In addition, the first ring portions 402a and 402b and the second ring portions 404a and 404b may be formed on the positions that allow the fixing part 200 to be disposed along the reinforcement member 30.

Figure 23:
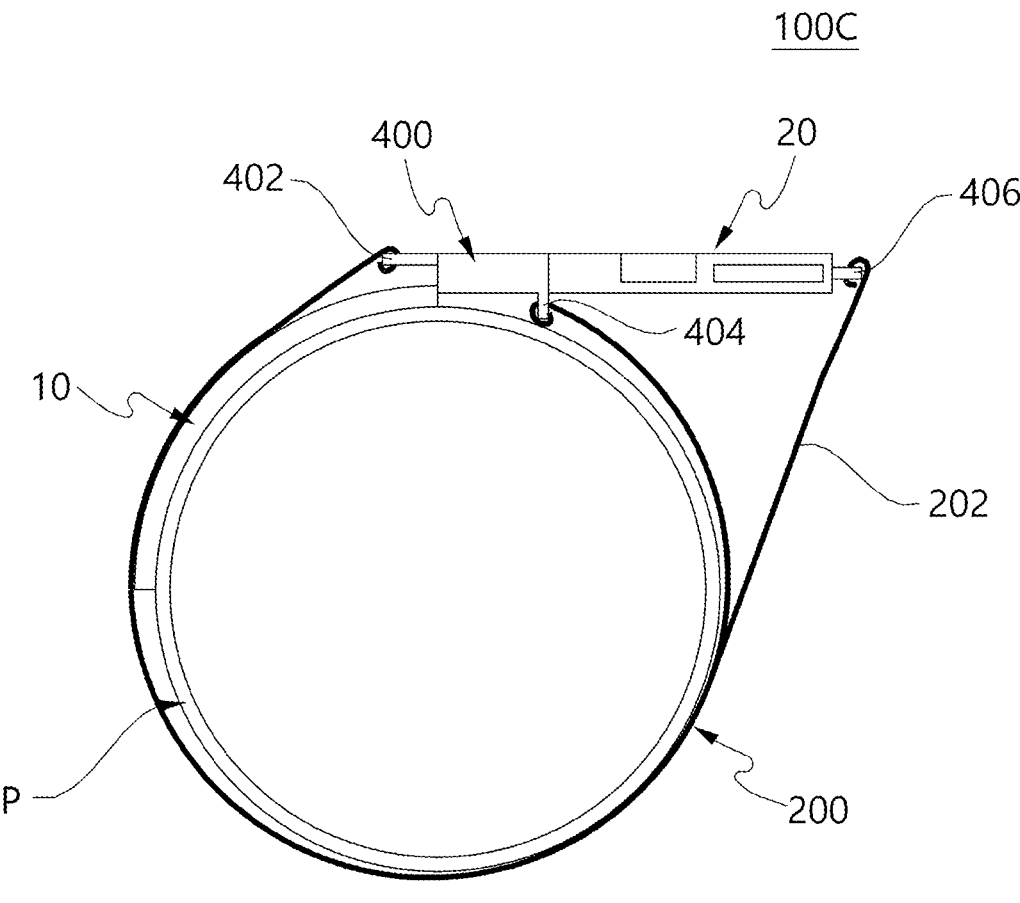
FIG. 23 is a view illustrating another embodiment in which the detector according to the fourth embodiment of the present invention is mounted on a test target.

FIG. 23 is a view illustrating another embodiment in which the detector according to the fourth embodiment of the present invention is mounted on the test target.

With reference to FIG. 23, a third ring portion 406 is formed at a position on the second part 20 opposite to the first ring portion 402. The fixing part 200 may further include a branch portion 202, and an end of the branch portion 202 may be additionally fixed to the third ring portion 406. The branch portion 202, which branches off from the fixing part 200, may be additionally fixed to the third ring portion 406 formed on the second part 20, thereby preventing the second part 20 from swaying.

Figure 24:
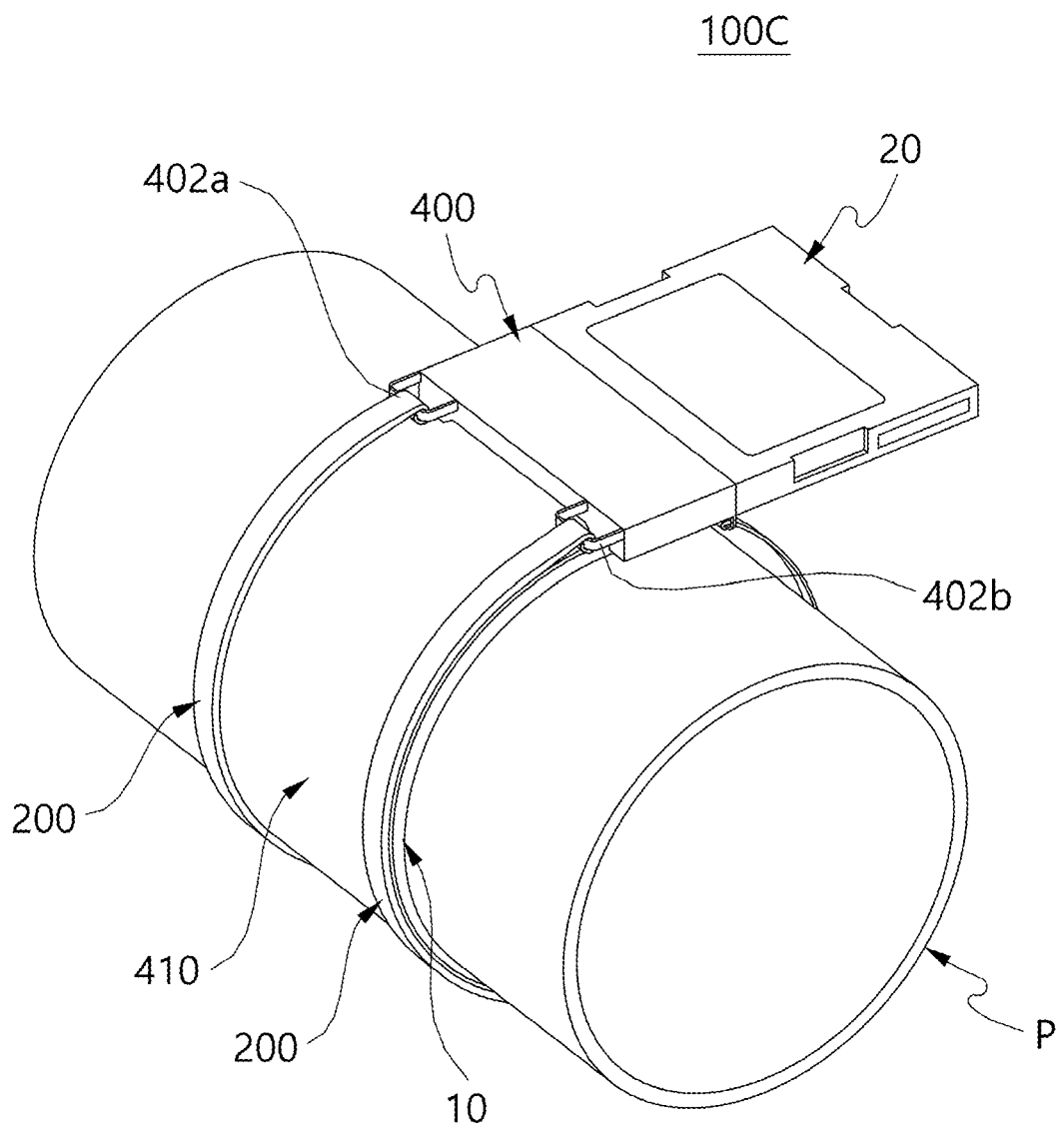
FIG. 24 is a view illustrating still another embodiment in which the detector according to the fourth embodiment of the present invention is mounted on a test target.
Figure 25:
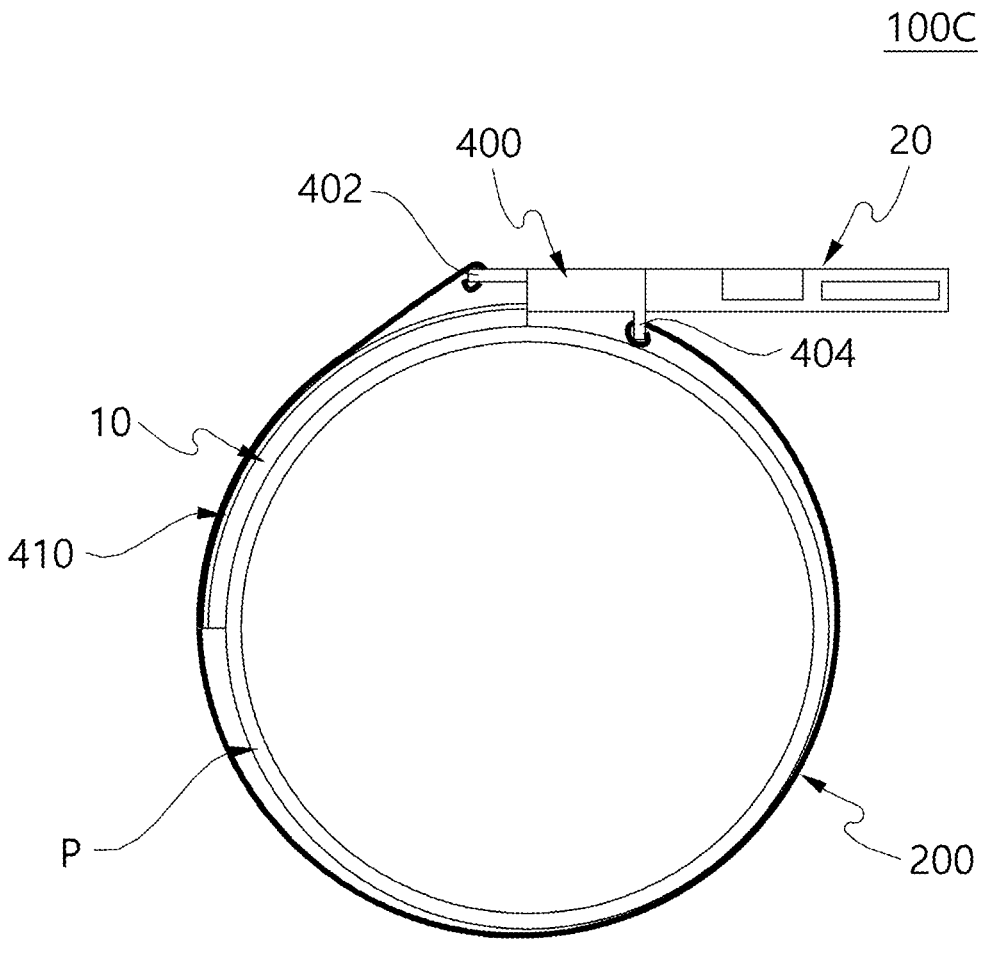
FIG. 25 is a side view illustrating still another embodiment in which the detector according to the fourth embodiment of the present invention is mounted on a test target.

FIG. 24 is a perspective view illustrating still another embodiment in which the detector according to the fourth embodiment of the present invention is mounted on the test target, and FIG. 25 is a side view illustrating still another embodiment in which the detector according to the fourth embodiment of the present invention is mounted on the test target.

In case that the first part 10 is fixed to the test target P by using the fixing part 200, the surface of the first part 10 having the elasticity may not be completely tightly attached to the test target P. In order to cope with this situation, an auxiliary board 410, which has a surface with a predetermined curvature and is made of an elastic material, may be additionally provided.

The auxiliary board 410 is disposed above the first part 10, and the auxiliary board 410 assists in tightly attaching the first part 10 to an outer peripheral surface of the test target P. The fixing part 200 is fixed onto an outer surface of the auxiliary board 410. The auxiliary board 410 may be configured as a metal board made of an elastic material or a board made of a carbon composite, synthetic resin, rubber, or silicone.

Figure 26:
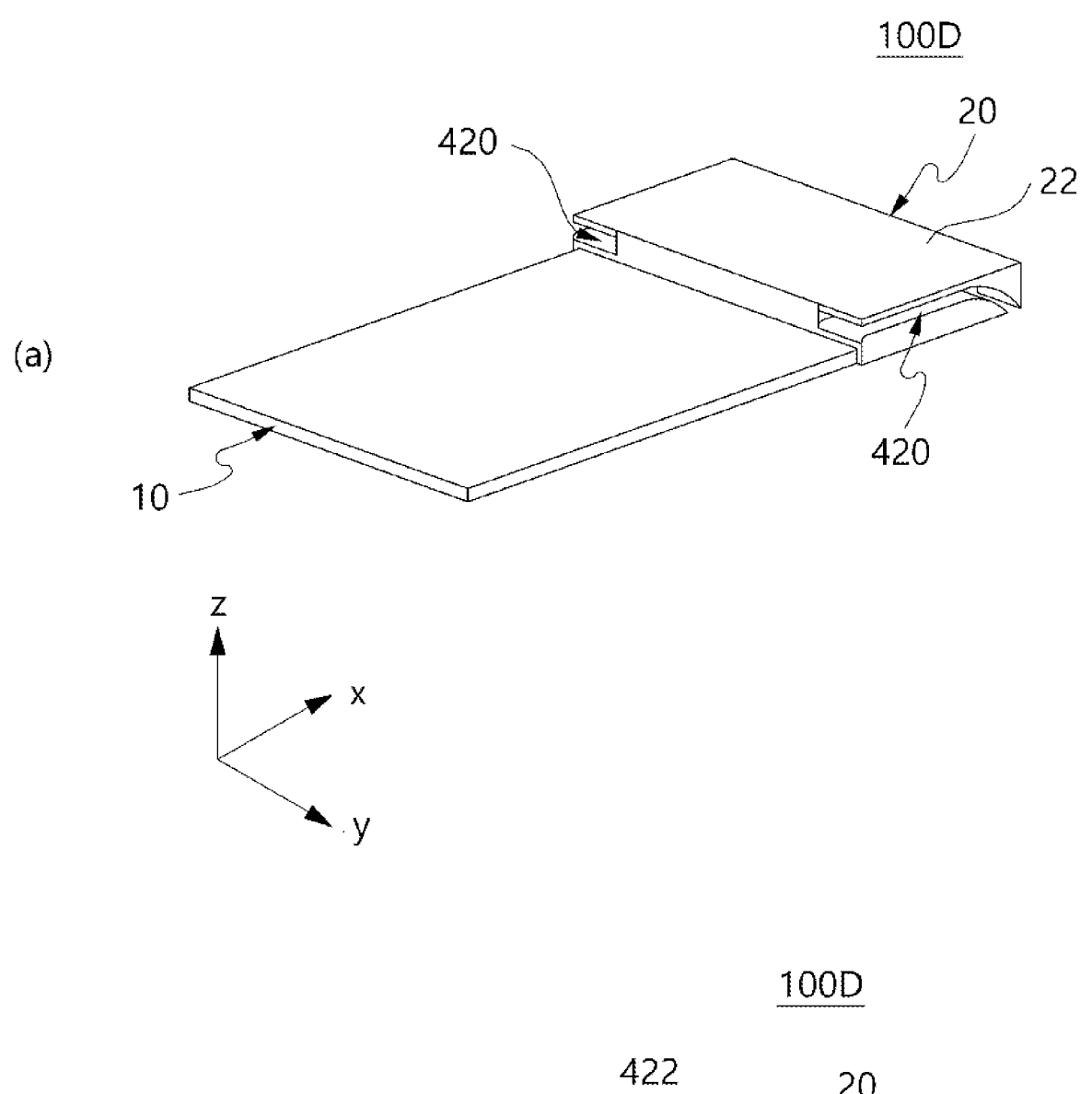
FIG. 26 is a view illustrating a detector according to a fifth embodiment of the present invention.
Figure 27:
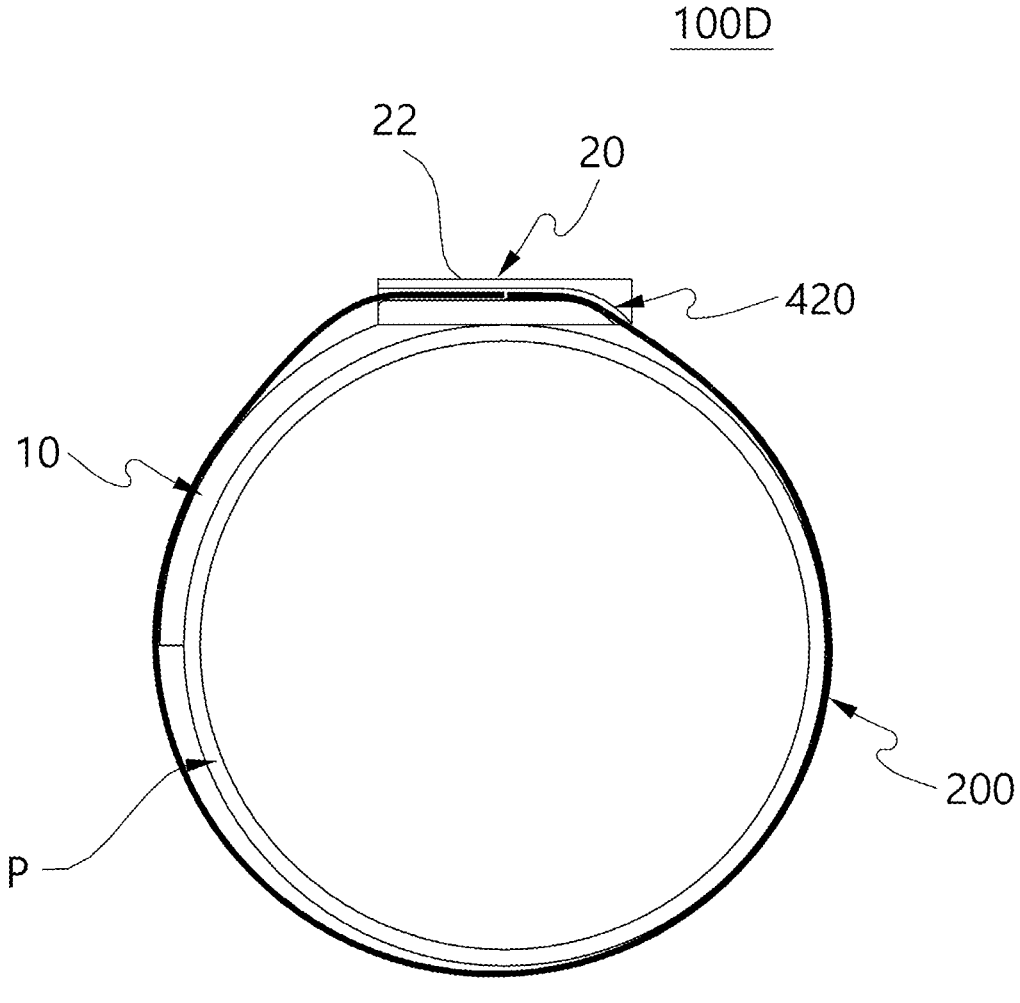
FIG. 27 is a view illustrating a state in which the detector according to the fifth embodiment of the present invention is mounted on a test target.

FIG. 26 is a view illustrating a detector according to a fifth embodiment of the present invention (part (a) of FIG. 26 is a perspective view, and part (b) of FIG. 26 is a side view), and FIG. 27 is a view illustrating a state in which the detector according to the fifth embodiment of the present invention is mounted on the test target.

A detector 100D according to the fifth embodiment of the present invention is identical to the detectors 100, 100A, 100B, and 100C in the other embodiments in that the detector includes the first part 10 and the second part 20.

Fixing part passage grooves 420 for the fixing part 200 may be formed at two opposite ends of the second housing 22 that constitutes the second part 20 of the detector 100D according to the fifth embodiment. The fixing part passage grooves 420 may be opened toward the two opposite sides. However, the fixing part passage grooves 420 may be opened only in a forward/rearward direction (approximately X-axis direction) and closed in two opposite lateral directions (Y-axis direction).

The fixing part 200 may fix the first part 10 to the test target P while passing through the fixing part passage groove 420, and the second part 20 may also be fixed to the test target P.

In the embodiment, with reference to part (b) of FIG. 26, the fixing part passage groove 420 may include a first passage groove 422 formed straight in a direction toward the first part 10, and a second passage groove 424 formed to have a predetermined curvature in a direction opposite to the first part 10 and extending from the first passage groove 422.

The above description is simply given for illustratively describing the technical spirit of the present invention, and those skilled in the art to which the present invention pertains will appreciate that various modifications, changes, and substitutions are possible without departing from the essential characteristic of the present invention. Accordingly, the embodiments disclosed in the present invention and the accompanying drawings are intended not to limit but to describe the technical spirit of the present invention, and the scope of the technical spirit of the present invention is not limited by the embodiments and the accompanying drawings. The protective scope of the present invention should be construed based on the following claims, and all the technical spirit in the equivalent scope thereto should be construed as falling within the scope of the present invention.

The invention claimed is:

1. A detector, comprising:
a first part including a first housing and a detection panel, the first housing including an elastic material, the detection panel being disposed in the first housing;
a second part connected to the first part and including a second housing, the second housing including an inelastic material or a material having higher rigidity than the elastic material of the first housing; and
a reinforcement member disposed outside the detection panel and disposed in the first housing, the reinforcement member surrounding at least a part of the detection panel on a horizontal plane perpendicular to a thickness direction of the detection panel,
wherein the first housing comprises:
a panel accommodation portion configured to accommodate the detection panel; and
a reinforcement member accommodation portion defined outside the panel accommodation portion when viewed on the horizontal plane, the reinforcement member accommodation portion being configured to accommodate the reinforcement member,
wherein the reinforcement member comprises a first reinforcement portion disposed in a first accommodation region of the reinforcement member accommodation portion in a first direction, and
wherein the first reinforcement portion is configured to move in the reinforcement member accommodation portion in the first direction on the horizontal plane when the first part is bent.

2. The detector of claim 1, wherein the reinforcement member includes a connection portion coupled to one end of the second housing at which the first housing and the second housing are connected.

3. The detector of claim 1, wherein the reinforcement member extends across the first housing and the second housing.

4. The detector of claim 3, wherein the reinforcement member includes a connection portion coupled to an inside of the second housing.

5. The detector of claim 1,
wherein the reinforcement member further comprises:
a second reinforcement portion disposed in a second accommodation region of the reinforcement member accommodation portion in a second direction perpendicular to the first direction, and
wherein the second reinforcement portion is configured to move in the reinforcement member accommodation portion in the second direction on the horizontal plane when the first part is bent.

6. The detector of claim 1,
wherein the first reinforcement portion includes a protruding portion protruding from one end of the first reinforcement portion in a vertical direction with respect to the horizontal plane or protruding from one end of the first reinforcement portion to have a predetermined angle with respect to the vertical direction,
wherein the first accommodation region includes a stopper portion configured to come into contact with the protruding portion in the first direction when the first reinforcement portion moves in the first direction on the horizontal plane, and wherein the protruding portion and the stopper portion are configured to be in contact with each other in a state in which the first part is maximally bent in the first direction.

7. The detector of claim 1, wherein the first housing comprises:
a first plate disposed on one surface of the reinforcement member; and
a second plate disposed on another surface of the reinforcement member opposite to the one surface of the reinforcement member in a vertical direction with respect to the horizontal plane.

8. The detector of claim 7, further comprising:
a bending restriction part configured to restrict a degree to which the first part is maximally bendable,
wherein the bending restriction part is disposed in a bending restriction part guide portion defined in the reinforcement member in the first direction on the horizontal plane, and
wherein the bending restriction part is configured to move in the first direction on the horizontal plane along the bending restriction part guide portion when the first part is bent.

9. The detector of claim 8, wherein the bending restriction part guide portion comprises a pair of bending restriction part guide portions defined in a second direction perpendicular to the first direction with the detection panel interposed therebetween.

10. The detector of claim 8, wherein the bending restriction part includes a protruding portion protruding from one end of the bending restriction part in the vertical direction or protruding from one end of the bending restriction part to have a predetermined angle with respect to the vertical direction, and the reinforcement member includes a stopper portion configured to come into contact with the protruding portion in the first direction when the bending restriction part moves in the first direction on the horizontal plane.

11. The detector of claim 1, wherein a fixing part passage groove is defined at a lateral end of the second housing, and a fixing part configured to fix the detector to a test target passes through the fixing part passage groove.

12. A detector, comprising:
a first part including a first housing and a detection panel, the first housing including an elastic material, the detection panel being disposed in the first housing;
a second part connected to the first part and including a second housing, the second housing including an inelastic material or a material having higher rigidity than the elastic material of the first housing; and
a reinforcement member disposed outside the detection panel and disposed in the first housing, the reinforcement member surrounding at least a part of the detection panel on a horizontal plane perpendicular to a thickness direction of the detection panel,
wherein the second part includes a first ring portion extending in a first direction, and a second ring portion extending in a second direction different from the first direction, and
wherein a fixing part configured to fix the detector to a test target is coupled to the first ring portion and the second ring portion.

13. The detector of claim 12, wherein the first ring portion is comprises a pair of first ring portions, the second ring portion is comprises a pair of second ring portions, and the pair of first ring portions and the pair of second ring portions are positioned at which the fixing part presses portions of the first housing disposed outside the detection panel.

14. The detector of claim 12, wherein a fixing block on which the first ring portion and the second ring portion are disposed is coupled to the second housing.

15. The detector of claim 13, wherein a fixing block on which the first ring portion and the second ring portion are disposed is coupled to the second housing.

16. The detector of claim 12, wherein a third ring portion is disposed at a side of the second housing opposite to the first part, and a branch portion, which branches off from the fixing part, is coupled to the third ring portion.

17. An imaging device comprising:
a detector;
a fixing part configured to fix the detector such that the detector is tightly attached to a test target; and
a radioactive ray generation part configured to be disposed inside or outside the test target and configured to emit radiation to the detector,

wherein the detector comprises:
a first part including a first housing and a detection panel, the first housing including an elastic material, the detection panel being disposed in the first housing;
a second part connected to the first part and including a second housing, the second housing including an inelastic material or a material having higher rigidity than the elastic material of the first housing; and
a reinforcement member disposed outside the detection panel and disposed in the first housing, the reinforcement member surrounding at least a part of the detection panel on a horizontal plane perpendicular to a thickness direction of the detection panel.

18. The imaging device of claim 17, further comprising:
an auxiliary board configured to press the first part of the detector toward the test target.

* * * * *